(12) United States Patent
Frieder et al.

(10) Patent No.: US 11,344,264 B2
(45) Date of Patent: *May 31, 2022

(54) METHOD OF AUTOMATED DETERMINATION OF HEALTH CONCERNS THROUGH ACTIVITY PATTERN ANALYSIS

(71) Applicant: AURA HOME, INC., San Francisco, CA (US)

(72) Inventors: Ophir Frieder, Chevy Chase, MD (US); Eric Jensen, Brooklyn, NY (US); Abdur Chowdhury, San Francisco, CA (US); Ben Cherry, San Francisco, CA (US); Matt Sanford, Seattle, WA (US)

(73) Assignee: AURA HOME, INC., San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/172,624

(22) Filed: Feb. 10, 2021

(65) Prior Publication Data

US 2021/0161483 A1 Jun. 3, 2021

Related U.S. Application Data

(63) Continuation of application No. 17/038,064, filed on Sep. 30, 2020, now Pat. No. 10,945,680, which is a
(Continued)

(51) Int. Cl.
*A61B 5/00* (2006.01)
*H04L 67/50* (2022.01)
(Continued)

(52) U.S. Cl.
CPC ............ *A61B 5/746* (2013.01); *A61B 5/1112* (2013.01); *A61B 5/1118* (2013.01);
(Continued)

(58) Field of Classification Search
CPC ..... A61B 5/746; A61B 5/1112; A61B 5/1118; A61B 5/1123; A61B 5/4866;
(Continued)

(56) References Cited

U.S. PATENT DOCUMENTS 8,633,853 B2   1/2014   Amidi
9,225,789 B2  12/2015   Jensen et al.
(Continued)

OTHER PUBLICATIONS

Hazas, M., et al., "Location-Aware Computing Comes of Age," Invisible Computing, Feb. 2004, pp. 95-97.
(Continued)

*Primary Examiner* — Michael A Keller
(74) *Attorney, Agent, or Firm* — Pauley Erickson & Swanson

(57) ABSTRACT

A method, system, and/or apparatus for automatically monitoring for possible mental or physical health concerns. The method or implementing software application uses or relies upon location information available on the mobile device from any source, such as cell phone usage and/or other device applications. The method and system automatically learns user activity patterns and detects significant deviations therefrom. The deviations are automatically analyzed for known correlations to mental or physical concerns, which can then be automatically communicated to a relevant friend, family member, and/or medical professional.

19 Claims, 17 Drawing Sheets

Related U.S. Application Data continuation of application No. 16/432,373, filed on Jun. 5, 2019, now Pat. No. 10,813,599, which is a continuation of application No. 16/046,590, filed on Jul. 26, 2018, now Pat. No. 10,314,550, which is a continuation of application No. 15/291,819, filed on Oct. 12, 2016, now Pat. No. 10,039,504, which is a continuation of application No. 14/848,881, filed on Sep. 9, 2015, now Pat. No. 9,498,163, which is a continuation-in-part of application No. 14/751,399, filed on Jun. 26, 2015, now Pat. No. 9,439,038, which is a continuation-in-part of application No. 14/270,534, filed on May 6, 2014, now Pat. No. 9,288,616, and a continuation-in-part of application No. 14/455,279, filed on Aug. 8, 2014, now Pat. No. 9,386,052, and a continuation-in-part of application No. 14/455,297, filed on Aug. 8, 2014, now Pat. No. 9,420,015, said application No. 14/270,534 is a continuation-in-part of application No. 14/051,071, filed on Oct. 10, 2013, now Pat. No. 9,225,789, and a continuation-in-part of application No. 14/051,089, filed on Oct. 10, 2013, now Pat. No. 9,338,759, said application No. 14/455,279 is a continuation-in-part of application No. 14/051,071, filed on Oct. 10, 2013, now Pat. No. 9,225,789, and a continuation-in-part of application No. 14/051,089, filed on Oct. 10, 2013, now Pat. No. 9,338,759, said application No. 14/455,297 is a continuation-in-part of application No. 14/051,071, filed on Oct. 10, 2013, now Pat. No. 9,225,789, and a continuation-in-part of application No. 14/051,089, filed on Oct. 10, 2013, now Pat. No. 9,338,759.

(51) Int. Cl.

| | | |
|---|---|---|
| *A61B 5/11* | (2006.01) | |
| *G06F 16/9535* | (2019.01) | |
| *G06F 21/55* | (2013.01) | |
| *H04L 51/222* | (2022.01) | |
| *H04L 51/52* | (2022.01) | |
| *H04L 51/58* | (2022.01) | |
| *H04W 4/02* | (2018.01) | |
| *H04W 4/12* | (2009.01) | |
| *H04W 52/02* | (2009.01) | |
| *G16H 40/63* | (2018.01) | |
| *H04W 4/21* | (2018.01) | |
| *H04W 4/029* | (2018.01) | |
| *G16Z 99/00* | (2019.01) | |
| *H04W 4/33* | (2018.01) | |
| *H04W 64/00* | (2009.01) | |
| *H04M 1/72454* | (2021.01) | |
| *H04L 51/08* | (2022.01) | |

(52) U.S. Cl.
CPC .......... *A61B 5/1123* (2013.01); *A61B 5/4866* (2013.01); *A61B 5/6898* (2013.01); *A61B 5/72* (2013.01); *A61B 5/7246* (2013.01); *A61B 5/7267* (2013.01); *A61B 5/7282* (2013.01); *A61B 5/742* (2013.01); *A61B 5/7455* (2013.01); *A61B 5/7465* (2013.01); *G06F 16/9535* (2019.01); *G06F 21/552* (2013.01); *G16H 40/63* (2018.01); *G16Z 99/00* (2019.02); *H04L 51/20* (2013.01); *H04L 51/32* (2013.01); *H04L 51/38* (2013.01); *H04L 67/22* (2013.01); *H04W 4/023* (2013.01); *H04W 4/029* (2018.02); *H04W 4/12* (2013.01); *H04W 4/21* (2018.02); *H04W 4/33* (2018.02); *H04W 52/0229* (2013.01); *H04W 52/0254* (2013.01); *G06F 2221/2111* (2013.01); *H04L 51/08* (2013.01); *H04M 1/72454* (2021.01); *H04W 64/006* (2013.01); *Y02D 30/70* (2020.08)

(58) Field of Classification Search
CPC ....... A61B 5/6898; A61B 5/72; A61B 5/7246; A61B 5/7267; A61B 5/7282; A61B 5/742; A61B 5/7455; A61B 5/7465; G06F 16/9535; G06F 21/552; G06F 2221/2111; G16H 40/63; G16Z 99/00; H04L 51/20; H04L 51/32; H04L 51/38; H04L 67/22; H04L 51/08; H04W 4/023; H04W 4/029; H04W 4/12; H04W 4/21; H04W 4/33; H04W 52/0229; H04W 52/0254; H04W 64/006; H04W 4/02; H04M 1/72454; Y02D 30/70

See application file for complete search history.

(56) References Cited

U.S. PATENT DOCUMENTS

| | | |
|---|---|---|
| 9,288,616 B2 | 3/2016 | Cherry et al. |
| 9,338,759 B2 | 5/2016 | Chowdhury et al. |
| 2007/0282621 A1 | 12/2007 | Altman et al. |
| 2008/0201638 A1 | 8/2008 | Nair |
| 2009/0240586 A1 | 9/2009 | Ramer et al. |
| 2009/0286549 A1 | 11/2009 | Canon |
| 2009/0316671 A1 | 12/2009 | Rolf et al. |
| 2010/0030612 A1 | 2/2010 | Kim et al. |
| 2010/0082398 A1 | 4/2010 | Davis et al. |
| 2010/0130233 A1 | 5/2010 | Parker |
| 2010/0280904 A1 | 11/2010 | Ahuja |
| 2010/0298899 A1 | 11/2010 | Donnelly et al. |
| 2010/0332324 A1 | 12/2010 | Khosravy et al. |
| 2010/0332326 A1 | 12/2010 | Ishai |
| 2011/0029359 A1 | 2/2011 | Roeding et al. |
| 2011/0029370 A1 | 2/2011 | Roeding et al. |
| 2011/0161427 A1 | 6/2011 | Fortin et al. |
| 2011/0178863 A1 | 7/2011 | Daigle |
| 2011/0179064 A1 | 7/2011 | Russo |
| 2011/0238755 A1 | 9/2011 | Khan et al. |
| 2011/0313874 A1* | 12/2011 | Hardie ............... H04W 4/02 705/26.1 |
| 2012/0047129 A1 | 2/2012 | Redstone |
| 2012/0058782 A1 | 3/2012 | Li |
| 2012/0089679 A1 | 4/2012 | Gold |
| 2012/0158845 A1 | 6/2012 | Baalu et al. |
| 2012/0179563 A1 | 7/2012 | Soroca et al. |
| 2012/0215637 A1 | 8/2012 | Hermann |
| 2012/0265841 A1 | 10/2012 | Ross et al. |
| 2012/0270611 A1 | 10/2012 | Choi |
| 2012/0278387 A1 | 11/2012 | Garcia et al. |
| 2012/0290389 A1 | 11/2012 | Greenough et al. |
| 2012/0302258 A1 | 11/2012 | Pai et al. |
| 2012/0309376 A1 | 12/2012 | Huang |
| 2012/0316963 A1 | 12/2012 | Moshfeghi |
| 2013/0060640 A1 | 3/2013 | Gadhla et al. |
| 2013/0066964 A1 | 3/2013 | Odio et al. |
| 2013/0073622 A1 | 3/2013 | Nguyen et al. |
| 2013/0085861 A1 | 4/2013 | Dunlap |
| 2013/0103757 A1 | 4/2013 | Mitchell et al. |
| 2013/0117109 A1 | 5/2013 | Busch |
| 2013/0166386 A1 | 6/2013 | Simmons |
| 2013/0191215 A1 | 7/2013 | Metcalf |
| 2013/0203440 A1 | 8/2013 | Bilange et al. |
| 2013/0303106 A1 | 11/2013 | Martin |
| 2014/0081667 A1 | 3/2014 | Joao |
| 2014/0333432 A1 | 11/2014 | Armitage |
| 2014/0365507 A1 | 12/2014 | Wissner et al. |
| 2015/0058345 A1 | 2/2015 | Mishra et al. |
| 2015/0074721 A1 | 3/2015 | Fishman |
| 2015/0106448 A1 | 4/2015 | Ownbey et al. |
| 2015/0106449 A1 | 4/2015 | Cherry et al. |
| 2015/0373493 A1 | 12/2015 | Chowdhury et al. |

(56) References Cited

U.S. PATENT DOCUMENTS

| | | | |
|---|---|---|---|
| 2016/0066864 A1* | 3/2016 | Frieder | H04L 51/20 |
| | | | 600/300 |
| 2016/0128618 A1 | 5/2016 | Lee | |
| 2016/0140934 A1 | 5/2016 | Frieder et al. | |
| 2016/0196389 A1* | 7/2016 | Moturu | G16H 50/50 |
| | | | 705/2 |
| 2017/0027529 A1 | 2/2017 | Frieder et al. | |
| 2017/0188196 A1 | 6/2017 | Shen et al. | |
| 2018/0333108 A1 | 11/2018 | Frieder et al. | |
| 2019/0343467 A1 | 11/2019 | Frieder et al. | |
| 2021/0007680 A1 | 1/2021 | Frieder et al. | |

OTHER PUBLICATIONS

Chen, G., et al., "A Survey of Context-Aware Mobile Computing Research." Dartmouth Computer Science Technical Report TR2000-381, (2000), 16 pages.

Bahl, P., et al., "RADAR: An In-Building RF-based User Location and Tracking System," IEEE INFOCOM (2000), vol. 2, pp. 775-784.

Kennedy, M., et al., "Adaptive Energy Optimization in Multimedia-centric Wireless Devices: A Survey," IEEE Communication Surveys and Tutorials (COMST), (2012), 19 pages.

Wang, C., et al., "Simultaneous Localization, Mapping and Moving Object Tracking," International Journal of Robotics Research (2004), 47 pages.

Krumm, J., et al., "LOCADIO: Inferring Motion and Location from Wi-Fi Signal Strengths," MOBIQUITOUS Conference, Boston, MA, Aug. 22-26, 2004, pp. 4-13.

Perrucci, G. P., et al., "On the Impact of 2G and 3G Network Usage for Mobile Phones' Battery Life," European Wireless Conference (2009), May 17-20, pp. 255-259.

\* cited by examiner

Where and how did they spend their last 2 days of weekends days.

- Time spent at home is about less than a minute or 0.0% of their time.
- Time spent at work is about less than a minute or 0.0% of their time.
- Time in transit is about 9 hours or 18.06% of their time.
- Time at spent at other places 1 day or 81.94% of their time.

| Category | Time Spent | Location | Contexts |
|---|---|---|---|
| | about 15 hours | Barney, ND | ["on the farm"] |
| | about 10 hours | Breckenridge, MN | ["hanging with grandma"] |
| | about 9 hours | Georgetown, Washington | ["hanging at a hotel"] |
| | about 1 hour | The Shops at Wisconsin Place, Bethesda | ["at dinner"] |
| | about 1 hour | O'Hare, Chicago | ["At ORD"] |

Where and how did they spend their last 5 days of weekdays.

- Time spent at home is about 11 hours or 9.94% of their time.
- Time spent at work is about less than a minute or 0.0% of their time.
- Time in transit is about 9 hours or 16.32% of their time.
- Time at spent at other places 3 days or 73.75% of their time.

| Category | Time Spent | Location | Contexts |
|---|---|---|---|
| | 1 day | Georgetown, Washington | ["hanging at a hotel," "at the four seasons"] |
| | about 12 hours | Barney, ND | ["on the farm"] |
| | about 11 hours | | ["at home"] |
| | about 7 hours | | ["at ophir's"] |
| | about 7 hours | | ["hanging at a hotel"] |
| | ... | | |

FIG. 5

Summary of transit by speed:

- Slow travel (<5mph) is about 5 hours, 28.66 miles.
- Medium travel (>5mph, >100mph) is about 5 hours, 274.89 miles.
- Fast travel (>100 mph) is about 12 hours, 2703.57 miles.

| When | Distance | Time | Speed Mph | Mode | From | To |
|---|---|---|---|---|---|---|
| Jul/23 04:53 | 0.77 miles | 8 minutes | 5.84 | slow | at restaurant | home |
| Jul/23 01:21 | 0.77 miles | 20 minutes | 2.26 | slow | home | at restaurant |
| Jul/22 21:29 | 964.57 miles | about 3 hours | 291.29 | fast | Denver airport | home |
| Jul/22 18:11 | 626.88 miles | about 3 hours | 198.01 | fast | Hector International Airport, Fargo | Denver airport |
| Jul/22 15:44 | 44.83 miles | about 1 hour | 46.63 | medium | hanging with grandma | Fargo airport |
| Jul/22 00:42 | 2.03 miles | 15 minutes | 8.2 | medium | hanging with grandma | Wahpeton, ND |
| Jul/21 15:50 | 20.23 miles | about 3 hours | 6.48 | slow | on the farm | Breckenridge, MN |
| Jul/20 18:01 | 523.84 miles | about 3 hours | 174.65 | fast | At ORD | hanging with grandma |
| Jul/20 13:51 | 588.28 miles | about 3 hours | 204.3 | fast | Dulles International Airport, Chantilly | At ORD |

FIG. 6

Weekly Contexts: 22

- hanging at a hotel 9 times this week or 31.83% of their time – 1 day
- hanging with grandma 6 times this week or 11.06% of their time – about 12 hours
- on the farm 3 times this week or 16.11% of their time – about 18 hours
- at the four seasons 2 times this week or 3.4% of their time – about 4 hours
- at home 2 times this week or 10.26% of their time – about 11 hours
- at ophir's 2 times this week or 6.46% of their time – about 7 hours
- commuting 1 times this week or 1.26% of their time – about 1 hour
- At ORD 1 times this week or 1.18% of their time – about 1 hour
- at IAD 1 times this week or 0.69% of their time – about 1 hour
- denver airport 1 times this week or 0.12% of their time – about 1 hour
- …

FIG. 7

Time spent breakdown for the last: 7 days

- Time spent at home is about 11 hours or 7.02% of their time.
- Time spent at work is about less than a minute or 0.0% of their time.
- Time in transit is about 1 day or 16.83% of their time.
- Time at spent at other places 5 days or 76.15% of their time.

Time spent compared to their friends.

- Spends 0.14x less time at home then their friends.
- Spends 0.0x less time at work than their friends.
- Spends 1.53x more time in transit than their friends.
- Spends 2.45x more time at places then their friends.

FIG. 8

Contexts you share with your friends: time spent vs. your friends

- at the hotel — You 3.4% vs. your friends 0.01% of their time or 340.0x.
- at home — You 10.26% vs. your friends 73.71% of their time or 0.14x.

Things you spent time with 5 others in your network:

(1) Activities with Ben together.
  - Time together: 40 minutes, contexts at NYC office, at work, (5) Activities with Chris together.
  - Time together: about 5 hours, contexts hanging at a hotel, drinks with the boys, at Restaurant A, dinner with friends, hanging with friends, (3) Activities with Joe together.
  - Time together: about 3 hours, contexts hanging at a hotel, at the hotel lounge, at central, at dinner, at restaurant, (8) Activities with Ophir together.
  - Time together: about 12 hours, contexts at Restaurant A, having sushi, at Ophir's, at home, at Restaurant B, (2) Activities with Alexis together.
  - Time together: about 11 hours, contexts at home, People you have not seen in a week: 84.85% (26/33)
User3426676(Bob Smith), ...

People who have not interacted with you in a week: 66.67% (22/33)
User3478676(Mary Smith), ...

FIG. 9

| Activity | Duration |
|---|---|
| Working | 18:40 |
| Sleeping | 15:30 |
| Walking | 3:05 |
| Eating | 2:44 |
| Reading | 2:08 |

Duration Covered: 48 hours

Number of Activities: 5

Duration Period: 24 hours
Number of Periods: 3
Number of Activities: 3

| Activity | Duration |
|---|---|
| Chevy Chase, MD | 10:40 |
| Washington, DC | 7:10 |
| Potomac, MD | 2:05 |
| Bethesda, MD | 1:47 |
| Rockville, MD | 1:08 |

Duration Covered: 24 hours

Number of Locations: 5

Duration Period: 24 hours
Number of Periods: 7
Number of Locations: 2

| Community Member | Duration |
|---|---|
| Nancy Green | 6:25 |
| Albert Cho | 2:17 |
| Eric Jones | 2:17 |

Duration Covered: 12 hours

Number of Community Members: 3

Duration Period: 24 hours
Number of Periods: 3
Number of Members: 3

| Contact | Condition | Belief Score |
|---|---|---|
| Nancy Green | Depression | Medium |
| Self | Depression | Low |
| Self | Sedentary | Low |
| Nancy Green | Sedentary | Low |
| Physical Therapist | Sedentary | High |

METHOD OF AUTOMATED DETERMINATION OF HEALTH CONCERNS THROUGH ACTIVITY PATTERN ANALYSIS

CROSS REFERENCE TO RELATED APPLICATIONS

This application is a continuation of U.S. patent application Ser. No. 17/038,064, filed on 30 Sep. 2020, which is a continuation of U.S. patent application Ser. No. 16/432,373, filed on 5 Jun. 2019, which is a continuation of U.S. patent application Ser. No. 16/046,590, filed on 26 Jul. 2018, which is a continuation of U.S. patent application Ser. No. 15/291,819, filed 12 Oct. 2016, which is a continuation of U.S. patent application Ser. No. 14/848,881, filed 9 Sep. 2015, which is a continuation-in-part of U.S. patent application Ser. No. 14/751,399, filed 26 Jun. 2015, which is a continuation-in-part of each of: U.S. patent application Ser. No. 14/270,534, filed 6 May 2014, U.S. patent application Ser. No. 14/455,279, filed 8 Aug. 2014, and U.S. patent application Ser. No. 14/455,297, filed 8 Aug. 2014; each of which is a continuation-in-part of each of U.S. patent application Ser. No. 14/051,071, filed on 10 Oct. 2013, and U.S. patent application Ser. No. 14/051,089, filed on 10 Oct. 2013. The co-pending parent applications are hereby incorporated by reference herein in their entirety and are made a part hereof, including but not limited to those portions which specifically appear hereinafter.

FIELD OF THE INVENTION

This invention relates generally to automated health monitoring, and more particularly, to a method, system, and apparatus that automatically detects and informs of possible medical issues.

BACKGROUND OF THE INVENTION

Social media systems have permeated daily life. Information is collected, organized, and disseminated worldwide via informational collection and dissemination, micro-blogging and blogging services. Other social media are mobile and positional in nature and can be referred to as Mobile Positional Social Media (MPSM). As these systems focus on locations, mobile device implementations permeate the space. That said, however, while MPSM implementations are targeted to primarily execute on mobile devices, such as but not limited to smart-phones (e.g., Apple's iPhone, Google's Android), tablets (e.g., Apple's iPad, HP Touch-Pad), and laptop computers, they often support implementations for non-mobile environments such as but not limited to desktops and workstations, and large scale compute farms and cloud computing servers.

MPSM systems focus on locating users and notifying each other within their community of their respective locations or nearby content of interest. For example, Foursquare's application locates users and informs them of items of interest in their vicinity or the vicinity of their choice. Users are motivated to actively and manually "check-in" at their location with specificity rewarded. Rewards include "badges" and honors such as being named "Mayor." Additional enticements are group texting facilities as provided by the likes of BrightKite. Other MPSM include but are not limited to Gowalla, Loopt, Jaiku, Plazes, and Fire Eagle.

One limitation of MPSM systems is their reliance on global positioning systems (GPS). The use of GPS devices does typically simplify location tracking implementation; however, this comes at a significant energy cost. Since a significant portion of MPSM systems usage is via mobile devices, reducing energy consumption is critical.

Another limitation of current MPSM systems is their reliance on active users identifying their location and/or their activity at the location. Another limitation of current MPSM systems is the limited modes of informational guidance provided to the user. For example, no reminders or instructional commenting is provided. That is, users are not reminded of activities that fit their given location and context in a push manner; rather, user inquiry of locally available options is needed. Ideally, given location and context users are proactively pushed information that is immediately relevant to them. Additionally, activities that are nearby to their current location or will become available can likewise be identified.

The use of smartphone technology for medical applications is increasing. In August 2014, the Food and Drug Administration (FDA) cleared a smartphone device, Alive-Cor, that detects atrial fibrillation, a potential warning sign for heart failure and stroke. Additionally, Apple Corporation, in support of medical smartphone technology, recently developed an open-source tool kit to aid in the authoring of medical research applications. Also known in the art is the use of activity and trend detection using smartphone technology for medical applications. Recently, an Android based application called StudentLife was introduced at Dartmouth College. This application monitors smartphone use (e.g., text messaging, e-mail traffic, etc.) as well as additional activity (e.g., mobility and sleep patterns) to infer state of being. Automatic sensed, as well as interactive user probing, data were collected to determine potential stress.

There is thus a continuing need for and interest in improved mobile device-based systems and applications for medical applications.

SUMMARY OF THE INVENTION

This invention provides a method, system, and apparatus, such as embodied in a MPSM or other software application that automatically determines and/or detects abnormal behavior for the purpose of identifying health concerns. The method and system automatically determine and share locations and/or activities of a user, thereby learning activity patterns for the user. The application learns user activity over time, with the learning based upon user locations and/or context. The present invention generally provides methods and applications for a MPSM that automatically understands and informs the "who, what, when, where, and/or how" of a user and the user's community. For example, who are the user and their community with, what are the user and their community doing, where geographically are the user and their community, when are, and historically when were, the user and their community doing this, and/or how can users' behaviors be modified?

The invention relies on the automatically learned location and activity patterns of the individual user and/or her/his community members to detect any abnormal behavior, such as a significant deviation from the learned activity pattern. Such deviation in behavior can occur for many reasons, including those of medical concern, and can serve as an early indicator of potential smoldering conditions.

The invention includes a method of determining medical conditions of users participating in a social networking service. The method is executed by a computer system and includes: automatically monitoring destinations and user activities of a first user via a first electronic device of the first user; automatically learning activity patterns for the first user; automatically determining a deviation in the learned activity patterns; automatically analyzing the deviation to identify a significance of the deviation; automatically correlating the significance of the deviation to a possible medical condition; and automatically alerting the first user via the first electronic device or a second user via a second electronic device of the possible medical condition. Embodiments of this invention incorporate an inference engine to automatically detect, analyze, and/or correlate the deviation.

The invention further includes a method of determining medical conditions of users participating in a social networking service that includes: automatically monitoring destinations and user activities of a first user via a first electronic device of the first user; receiving user information comprising a first user activity for at least one of the destinations upon a user arriving at the at least one destination; automatically learning activity patterns for the first user activity by automatically associating the user information with the at least one of the destinations, automatically determining a user activity context for the first user activity, and automatically comparing a further context of each of a plurality of further user arrivals to the at least one of the destinations to the user activity context, wherein the activity patterns comprise an eating pattern or an exercise pattern, at a location and/or with one or more community members; automatically determining a decrease in occurrences of the first user activity over a predetermined time period; automatically analyzing the decrease to identify a deviation significance, wherein the decrease and/or the deviation significance is automatically determined using an inference engine, and analyzing the decrease comprises correlating the decrease to user locations and conditions of the current locations during the predetermined time period; automatically correlating the deviation significance to a possible medical condition; and automatically alerting the first user via the first electronic device or a second user via a second electronic device of a possible medical condition correlated to the deviation, wherein the second user is a medical professional, close community member, and/or community member engaged in a similar user activity.

In embodiments of this invention, the automatic monitoring of destinations and user activities of a first user via a first electronic device of the first user includes: automatically determining a corresponding context for each of the user activities at a first user visit to each of the destinations; automatically tagging each of the destinations with a corresponding one of the user activities and corresponding context information, and storing the tagged location in a location database; automatically updating the context information of the tagged location for each of a plurality of automatically determined further user visits at the destinations from the further context of each of the further user visits; and automatically associating the first user activity with corresponding destinations and the corresponding context information. Each of the first context, the second context, the further context, and the context information can include at least one of: a time of day, a day of a week, a calendar date, a preceding user activity to the user visits, a weather condition, people accompanying the user, or community member activity bias information for the destination.

The invention includes a method of automated learning location and activity patterns for a user and automated determination of medical concerns, such as through a social networking service. The method is executed by a software application stored and executed on one or more computers or data processor systems, such as a mobile device (e.g., phone, tablet, or laptop) and/or an application server (such as for connecting user communities). In one embodiment the method includes receiving user information about a destination, automatically associating the user information with the destination, learning activity patterns for a user, automatically sharing the user information in the social networking service upon further user arrivals at the destination prior to receiving any additional user information, automatically monitoring for or detecting deviations in the expected activity pattern, and automatically determining and reporting that the deviation is significant enough to warrant a health concern for the user.

The invention also includes a method and supporting system for determining potentially unhealthy or dangerous changes in activity patterns of users participating in a social networking service. The method is executed by a computer system and includes steps of: automatically and either periodically or continually tracking locations of member electronic devices of a plurality of members of a social media community of a first user; automatically displaying location information for each of the plurality of members on a first user electronic device; automatically determining by analysis a significant deviation in an activity pattern; and automatically communicating the occurrence of the triggering condition to the first user or a second user through a respective user electronic device. The analysis of the change in activity pattern desirably includes automatically determining context information about the location information for the user without manual input therefrom; automatically deducing as user information a location type and/or other potential reason for the change in activity pattern (e.g., vacation, working overtime, or mild illness).

The electronic message can be delivered to the user herself/himself on her/his mobile device (e.g., the message creating device or another mobile device of the user) or to one or more other user device(s), such as a close friend, family member, and/or a medical professional. In other embodiments of this invention, the second user is someone likely to reengage the user in the activity of the activity pattern, such as restarting an exercise pattern or spending more time alone or with friends.

The invention still further includes a computer server for providing a tracking and/or social networking service, such as operating the methods discussed herein. The computer server of one embodiment of this invention includes a tagging module configured to correlate user information to a user destination, a database module configured to store user information including user locations and user activities at the user locations, an inference engine, and a communication module configured to automatically share medical concerns and/or a user activity in the social networking service upon further user arrivals at a corresponding one of the user locations. The computer system can also include an association module configured to associate the user activity with the corresponding one of the user locations.

In embodiments of this invention, the system or application identifies locations, and over time, automatically "checks-in" not only the locations but what the locations imply in terms of potential activities of the user. That is, given a location and a user, the system desirably suggests what activity or activities the user typically partakes at that location. For example, if a user frequents a location in "Potomac," this location might be identified as "parents' home." Furthermore, at this home, a variety of activities might be common such as: "visiting parents," "drinking tea," "eating lunch," or "sampling wine." In embodiments of this invention, each time the user appears at that location, based on context, defined by elements of or surrounding the activity such as but not limited to time of day, day of week, immediately preceding activities, weather, surrounding people, etc., a set of likely occurring activities are identified. The user can be prompted with a list from which to select a subset of these activities or to identify a new activity. The invention can also include ranking a user's potential suggested activity based on context and presenting that ranked list to the user, or the user's community. The invention generally provides a learning component that can allow the manual inputs to become automatic prompts, which can become automatically issued notifications for the location based upon the context. The prompts can be issued through any known format, such as an application alert on the device or a text message to the user. The invention also supports the user changing activities for a given location at any time, and/or user implemented delay of the notification of a user's location or activity.

The invention can include the incorporation or creation of user communities and sub-communities, with such communities and sub-communities sharing information. Embodiments of the invention include automatically identifying a user's location and activity, and desirably notifying that user's community of that user's location. Particular embodiments of this invention provide one or more additional community functionalities including, without limitation, automatically identifying a user's activity and notifying that user's community of that user's activity, commenting on user activity and location report by user or community—with multiple and multimedia comments supported, supporting the "liking" of user activity by the community, supporting the user tagging of location, activity, or the pairing of location and identity—tagging can be textual or via any multimedia means, correlating the individual user's activity with the ongoing activity of others within the community, and/or correlating the individual user's activity with the past activities of others within the community.

One embodiment of this invention provides a method of and system for automated determining of locations and/or activities of a user participating in a social networking service. The method is executed by a MPSM computer system and automatically determines a positional destination of a user, automatically deduces as user information a location type and/or user activity of the positional destination, and automatically shares the user information as instructed in the social networking service. Deducing the user information is based upon context information about the positional destination, desirably with minimal or no input by the user. The context can include, without limitation, time-dependent information, past and/or current associated user information, past user and/or community information about the location, and/or third party information. The context can be used to at least reduce location types and/or user activities, for example, as a function of the past location type and/or user activity of the positional destination for a given time period.

Another limitation of current MPSM systems is their lack of individual and community activity summarization capability. That is, summary of the local user and community member activities and time durations are not available, neither to the local user nor to their community. This summarization can range from simple statistical aggregation to advanced correlations as derived by known techniques in the art. In embodiments of this invention, users are provided with summaries of their locations, durations at these locations, and activities at these locations. Furthermore, at the discretion of the local user, these summaries are made available to their community members. Particular embodiments of this invention provide one or more additional summarization functionalities including, without limitation, maintaining a history of user locations, activities, or combination thereof, correlating the individual user's activity with the past activities of the user, correlating the individual user's activity with the expected learned future activities of self, data mining behavioral patterns and suggesting alternatives to avoid obstacles, providing statistical aggregation of locations visited, providing derived summarization of locations visited, providing statistical aggregation of activities, providing derived summarization of activities, providing statistical aggregation and/or derived summarization of individuals (such as community members) encountered during a time period.

Other objects and advantages will be apparent to those skilled in the art from the following detailed description taken in conjunction with the appended claims and drawings.

BRIEF DESCRIPTION OF THE DRAWINGS

FIG. 5 illustrates a system view location summary of an individual user according to one embodiment of this invention.

FIG. 6 illustrates a system view transit summary of an individual user according to one embodiment of this invention.

FIG. 7 illustrates a system view activity summary of an individual user according to one embodiment of this invention.

FIG. 8 illustrates a system view time location breakdown in comparison to other users according to one embodiment of this invention.

FIG. 9 illustrates a system view a listing of activities shared with other users according to one embodiment of this invention.

DETAILED DESCRIPTION OF THE INVENTION

Figure 1:
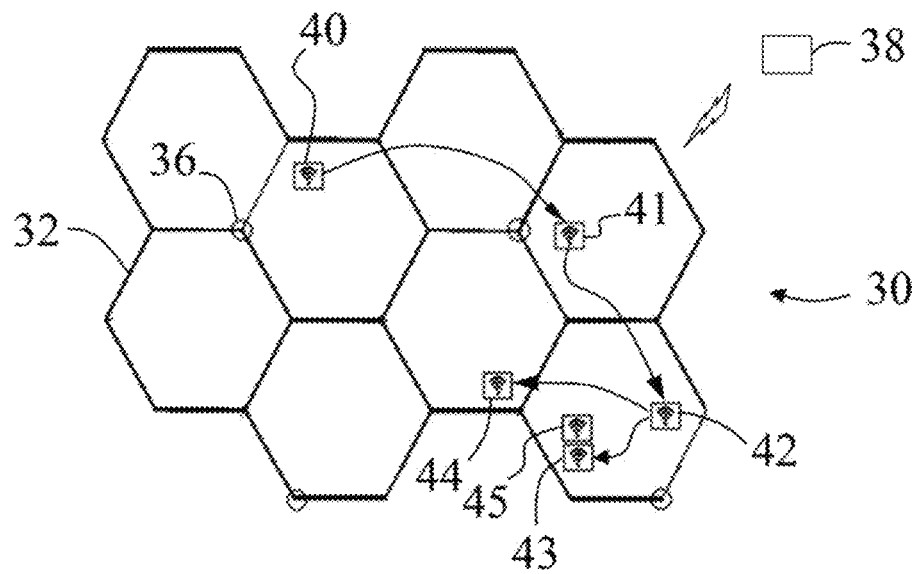
FIG. 1 shows a representative area of a user of one embodiment of this invention.

This invention includes a method, system, and/or apparatus, such as embodied in a MPSM or other software application that automatically determines and shares a location and/or an activity of a user. The automatic and continual determination of locations and/or activities of users participating in a social networking service allows for learning behavior patterns, and more particularly activity patterns, such as location visits, activities performed at the locations, and any community presence at those activities. As a brief example, upon repeated Friday morning tennis at the club with John, the systems learns that the user is playing tennis on Friday mornings if the system detects that the user is at the club and/or the user is with John. The invention merges this technology with health care monitoring, by using the learned patterns to analyze and detect behavior patterns that correlate to a potential health or medical concern. Using the example above, if the user stopped playing tennis with John, and/or stopped going to the club or performing any exercise, then there may be a potential health concern.

As such, the invention relies on automatically learned location and activity patterns of an individual and her/his community members to detect abnormal behavior. Such deviation in behavior can occur for many reasons, including those of medical concern and can serve as an early indicator of potential smoldering conditions. Without intending to be so limited, the invention is described below for brevity with reference to a non-limiting exemplary condition, namely depression. It is, however, within the scope of this invention, to detect, via MPSM technology, other ailments that exhibit symptoms detectable using inference from automatically learned location and activity, including other mental health issues, such as addictions or bi-polar issues, and/or physical health concerns, such as heart health concerns and weight-related concerns. The invention can also be used for monitoring behavior patterns to determine if someone is not taking medication, or otherwise following a treatment plan. The MPSM technology and method of this invention can also be paired with other electronic monitoring systems, such as electronic pulse or other fitness related monitors, particularly wearable devices, via wireless communication.

In embodiments of this invention, the application learns user activity over time, with the learning based upon user locations and/or context. The application can learn through automatically determining activities at locations based upon known context information and past context information for the location. The invention further includes energy saving location methods for the mobile device that can be used to more efficiently allow the location and social media aspects of the invention to be implemented on a mobile device. The method and application can be used for any suitable function, such as a safety and/or reminder serves, and is particularly useful for use in social media applications. The invention will be described below with implementation in a MPSM system, and particularly with an MPSM application that learns user activity over time, with the learning based upon user locations and/or context.

The method and system of this invention is mobile and positional in nature. Such systems, like many other systems originally developed on one type of computing platform but migrated to another, operate not only on mobile environments. That is, while MPSM implementations are targeted to primarily execute on mobile devices, such as but not limited to smart-phones, tablets, and/or laptops, they often support implementation for non-mobile environments such as but not limited to desktops and workstations, servers, and large scale compute farms and cloud computing servers. The invention will be described below with a mobile device, such as smart phone having cell service, a GPS system, and access to the Internet via WiFi.

The method and system of this invention is desirably executed or implemented on and/or through a mobile device computing platform. Such computing platforms generally include a processor, a recordable medium, an input/output (I/O) device, and a network interface capable of connecting either directly or indirectly to the Internet. The mobile device executes over a networked environment, a non-limiting example shown in FIG. 1. The mobile device is connected, either directly or indirectly, using any of the many techniques and technologies known in the art, over a network, to back-end system or systems, itself/themselves computing devices. The mobile device can connect with a remote server, shown in FIG. 1 as server 38, to store and/or access user or community information.

MPSM systems are used to support users remaining socially aware of their community. That is, their primary usage typically is to actively monitor the location and activity of family members, friends, colleagues, and generally others within one's community. Communities can be partitioned into sub-communities where the union of the sub-communities forms the user's community. The sub-communities may or may not overlap. The partitioning of communities into sub-communities is beneficial in supporting specialized applications. For example, while a user might have general interest in the location and activity of all of their community members, they might be particularly interested in the location and activity of those who might be suddenly in need of assistance.

Regardless of the community size, besides tracking users to potentially provide immediate assistance, medical environments that support state-of-being can capitalize on MPSM systems. State-of-being applications can detect abnormal patterns in a user's behavior or physical presence. By learning typical behavior of an individual regularly using a MPSM system according to embodiments of this invention, abnormality in behavior can be detected, and an alarm issued. It is within the scope of this invention to additionally incorporate data and information from health monitoring applications known in the art that are likewise resident on the mobile device to support state-of-being applications. Similarly, in community activities that require continuous monitoring and coordination, such as but not limited to an emergency response team or a neighborhood watch or other surveillance efforts, MPSM systems according to this invention can provide the necessary infrastructure to support the needed synchronization.

The creation of a community can include the issuing of invitations. An invitation is a request by a user A of another user B to allow the inviting user, user A, to track the activities of the invited user, user B, and vice versa. If the invited user accepts, the inviting and invited users form a community.

A community is relevant to only that user which formed it. That is, different users have different communities. A community is a grouping of invited (referred to as remote) users by the inviting (referred to as local) user. A local user can partition or merge a community, thus forming a sub-community or a parent community, respectively. For example, consider 5 users: Bob, Sam, Sally, Alice, and Susan. Bob can invite Sam, Sally, and Alice, thus forming his user community. Bob can likewise partition his community into a sub-community consisting of only Sam and Sally. Sally can invite Susan. Thus, Sally's community would include Bob (via his invitation) as well as Susan. If no additional invites occurred, Sam's and Alice's respective communities would only include Bob (each via Bob's invitation), while Susan's community would only include Sally (via Sally's invitation).

Providing users with the opportunity to expand their communities in a convenient manner is advantageous. Such expansion can seamlessly be accommodated by including users listed in a user's contact lists either as a whole or selectively into their community. Contact lists include, but are not limited to, users listed in a user's local address book, e-mail contact list, Twitter follow list, LinkedIn connections list, and/or Facebook friends list. By incorporating users listed in a user's contact list, the user's community is expanded without effort. Note, however, that selected inclusion can be supported; thus enabling community growth without unnecessarily over-expanding the community. That is, entries from the contact list can be included in their entirety and the user can selectively remove those entries which s/he wishes to be excluded from the community. Similarly, entries from the contact list can be selectively added.

Users are identified by their account identifier. To use MPSM a user account is created. User accounts generally require a user login, which is a unique user identifier, and a password or equivalent. After having created an account, a user can log in. Initially, the local user does not have a community. In embodiments of this invention, over time, the method and application tracks the activities and location of the local user. Should the local user establish a community as aforementioned described, the community members will likewise be tracked. Local users receive notifications of the location and activities of their community members. Once logged in, the local user can select to activate or deactivate self and community tracking and notification. If not overwritten, default settings are used.

Whenever logged in and tracking is enabled, a user's location and activity is tracked. That is, a user periodically records their location and/or activity. Locations are tagged by name. Names can be but are not limited to the following schemes: physical (e.g., 123 Oak St.), absolute (e.g., Acme Coffee), and/or relative (e.g., my work office), or proximity (e.g., two miles from home). Activities are typically events. These events might be common to the entire community such as: "drinking coffee," "eating lunch," "sampling wine," "working from home," "commuting," etc., to more specific to a local user such as "restoring car" or "driving to lake home." Multiple activities can occur simultaneously. Users can change their activities at any time.

Unless preloaded or derived from an external source, such as but not limited to a location database, initially, all locations and activities are unknown. Local users must record all such location-activity combinations, i.e., a local user must name or tag the location and the associated activity. A list of activities common to the local user's community can be provided. This community activity list can be ranked either arbitrarily (randomly), according to most recently used, most frequently used, relevance to location, alphabetically, etc. Eventually, an activity list specific to the local user is learned. This local user activity list can be displayed to the local user either individually, along with the community list, or merged with the community list. Again, any of these lists can be ranked as previously mentioned.

FIG. 1 illustrates a representative area 30 to demonstrate a method of and application for locations and/or activities of a user participating in a social networking service. The area 30 is shown as a cellular communication network including a plurality of cells 32 each disposed around a cellular communication antennae or base station 36. Within the area are a plurality of destinations each shown as including a WiFi Internet connection. The local user has one or more electronic devices, such as a mobile device that communicates with a remote server 38 via the cellular network and/or the WiFi connections. As will be appreciated the methods and applications of this invention can operate within any suitable size and configuration of the communication area, depending on what the user encounters.

Destination 40 is the home of the user. The user commutes to office 42 for work on most business days. On the way the user typically stops at the coffee shop 41. For lunch on most days, the user visits restaurant 43, but on Wednesdays the user typically meets a second user for lunch at restaurant 44.

At each destination 40-44, the user enters user information about the destination. The application and computer system that receives the user information automatically associates the user information with the destination, and stores the user information in a locations database, such as on the device and/or at server 38. The destination desirably is determined automatically and tagged with the user information, such as a location name of the destination and/or the user activity being performed at the destination. For example, destination 40 can be tagged as "home" and likely has numerous activities associated with it. The destination 41 can be tagged as its establishment name "Acme Coffee" or simply "coffee shop" and associated with the user activity of "buying coffee" or "latte time." The manually entered user information can then be automatically shared to the user's community in a social networking service. Similar user information is received for the other destinations 42-44. The user information desirably includes any other information about the location or activity, whether manually entered or automatically determined, such as the time of the visit or activity. Some destinations, such as home or work will likely have multiple user activities over a period of time, such as "coffee break," "meeting time," and/or "quitting time."

The computer system receives user information and associates the user information with the corresponding destination for multiple visits to each of the destinations 40-44. The computer system begins learning the locations and user activities. In embodiments of this invention, the user can be automatically prompted for confirmation of the user information upon arriving at a destination to confirm the location and/or user activity. For example, the user can be provided with an automatically generated list of previously entered user activities for the destination upon arrival, thereby promoting efficient collection of information. The items on the list can be listed in an order based upon a particular ranking, such as number of times entered previously or based upon a context, such as what activity is likely being performed at a particular time of a particular day.

Over time, the computer system learns the user information and begins automatically associating and identifying at least some user activities for corresponding locations. As will be appreciated, the automatic identifying of activities at locations will likely occur at different rates for different activities and locations, with some locations having fewer activities and/or more frequent visits than others. In preferred embodiments of this invention, the system automatically shares the user information in a social networking service upon automatically detecting further user arrivals at the destination. The automatic sharing of user locations and/or activities desirably occurs upon the user's arrival at the location, or at a particular time at the location. As such the invention includes an automatic detection of the user's arrival at a destination. The automatic sharing desirably operates without user action and prior to receiving any additional user information for the destination.

As an example, the user may typically purchase lunch at destination 43, but on Wednesdays typically goes to lunch with a friend or spouse at destination 44. The lunch routines of the user, and particularly the Wednesday lunch routine, can be learned by the system and automatically shared to the user's community upon the system automatically determining arrival, without manually input from the user. If the user is having lunch with a community member, then the system can automatically determine that both users are at the same location together to automatically recognize and confirm the lunch activity, and proceed to automatically share the information for both user's to their respective communities. If the user deviates from a routine, the system can know this, and refrain from sharing the typical destination, by the mobile device detecting a different location than the typical routine destination.

In embodiments of this invention, learning is accomplished by any known machine learning, data mining, and/or statistical techniques known in the art. Supervised, semi-supervised, and/or unsupervised approaches can be used, including, but not limited to Naïve Bayes, Neural Networks, Support Vector Machine, and/or Associating Mining based techniques.

The invention desirably records all posted locations and activities. Throughout use, the disclosed invention learns the corresponding locations and the set of associated activities. More so, via comments made by the local user and by the local user's communities, the importance of the activities can be learned, such as for the prompting discussed above. Importance can be either local user or community biased. Additionally, importance can be biased by context. For example, community members as a whole might prefer "eating steak," "eating pizza," and "eating sushi," in that respective order. On the other hand, a local user might only eat sushi. Thus, local user bias will yield "eating sushi" only, while community bias will suggest "eating steak," "eating pizza," and "eating sushi," in that respective order.

In embodiments of this invention, locations are named according to a naming convention. Regardless of the naming convention used, a location is a physical geographical position. More so, physical geographic locations associate properties that can vary with or be dependent on context, namely time and date (hours, day of week, calendar date, etc.), users involved, and their relationships to each other, etc. This context can affect the associated location name or activity.

A common scheme that can be used to at least assist in identifying a physical geographical location is via the use of geocoding. Geocoding is the representation of a physical location via the pairing of latitudinal and longitudinal coordinates commonly referred to as a lat-long pair. Global Positioning Systems (GPS) can also determine a physical position coordinated via the triangulation of satellite transmissions. Typically GPS devices derive lat-long pairs which are made available to a variety of applications, often via map displays. GPS economics, accuracy, and simplicity of use resulted in their wide appeal and commercial success. Their continuous use in mobile devices is problematic, however, as they are energy intensive and rapidly drain the battery. Thus, alternative means or approaches to detect locations are desired.

Embodiments of this invention, as discussed above in FIG. 1, use or rely upon cell coordinates. When mobile devices communicate with a cell tower, they send their cell coordinates. These coordinates are recorded by the cell provider and are typically not publicly known. The cell phone or, in this case, the mobile device supporting the positional social media system, however, is aware of their coordinates. Thus, the device can store the cell coordinate position and automatically associate that cell coordinate with the location name provided by the local user. Over time, a location database of cell coordinate and named location pairs is created. The local portion of the database favors the local user. The union of all the local portions of the location database desirably constitutes the name space of the entire MPSM system of this invention. It is understood that any of the many database management systems or storage schemes known in the art can serve as the platform for this location database. Thus, location names can be provided without the need to rely on a global positioning system, reducing battery consumption. Location data can additionally or alternatively be purchased or otherwise provided by a third party.

An additional and/or alternative approach for automatic location determination relies on WiFi triangulations. Mobile devices can grow and maintain a database of known open WiFi networks, for clarity we call this database an Open-WiFi-Net database. Such mobile devices can use the information stored or derived from the information stored in the Open-WiFi-Net database to further refine the accuracy of a location without the use of GPS. Via point triangulation, when an Open-WiFi-Net database is available, the mobile operating system uses not only the cell tower but also WiFi triangulations to determine location. It is within the scope of this invention to use either or both cell-phone and WiFi triangulations to enhance location information in addition to any other disclosed approach. The mobile device can use the WiFi signal at a destination, such as destination 43, and additionally or alternatively any detectable open WiFi signal from a neighboring location, such as establishment 45 that is adjacent destination 43.

Having created the location database, searching, namely querying, the database uses the cell coordinate or the location name. That is, a location name query takes a location name as input and returns the corresponding cell coordinate. A cell coordinate query takes a location name as input and returns the corresponding location name. Note that, multiple names can be attributed to a given cell coordinate. That is, a local user might name a location using multiple different names; different users can name same locations using different names. Similarly, the same name can be used for different cell coordinate locations. All names corresponding to a given cell coordinate are returned. It is within the scope of this invention to selectively return names based on context, user, or community bias. Similarly, all cell coordinates corresponding to a given name are returned. Again, it is within the scope of this invention to selectively return coordinates based on context, user, or community bias. Ranking of the results returned can, when desired, be biased towards the local user.

A key concern for MPSM systems is collecting location information. Clearly any location information available within the mobile device should be harnessed. Thus, if GPS readings or any other location information is generated by other device resident applications, these readings are desirably recorded and utilized by the method and application of this invention. However, reliance on strictly other applications to obtain positional information is obviously not realistic or possible.

In embodiments of this invention, positional information is obtained via the use of geofences. A geofence is geographical boundary or "fence" surrounding a positional reading. As these boundaries are radius based, geofences are generally circular. Location transmission occurs whenever a handover of one cell tower to another occurs and is expected but not guaranteed to occur once a geofence boundary is crossed. To track location, periodic location transmissions are required. Since location transmissions must be minimized to conserve device energy, transmissions should only occur given geographical movement. Thus, crossing a geofence should generate such a transmission. Unfortunately, as crossing a geofence does not guarantee a location transmission, increasing the likelihood of a transmission is necessary.

In contrast to the known uses that surround a location with a single geofence, to increase the likelihood of a location transmission during movement, embodiments of this invention include surrounding a location geofence with a plurality of geofences. In one embodiment of this invention, a method of tracking a user includes determining a location of the mobile user, automatically establishing a first geofence around the location, and automatically establishing a plurality of additional geofences around the first geofence, with each geofence including a boundary. A location transmission is obtained by the mobile device upon crossing a boundary of the first geofence or any of the plurality of additional geofences. Multiple neighboring geofences are advantageous since they increase the likelihood of a location transmission as their boundaries are likewise likely to be crossed given movement.

Figure 2:
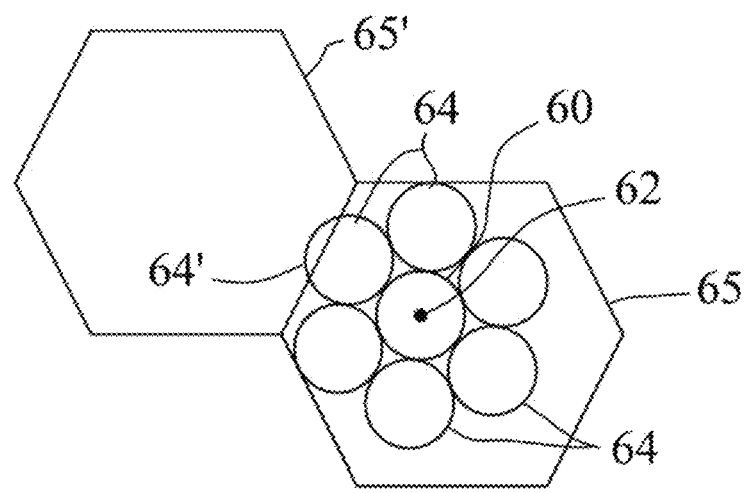
FIG. 2 illustrates geofences surrounding a current reading and its immediate neighbors according to one embodiment of this invention.

FIG. 2 representatively illustrates a geofence 60 surrounding a current location 62. The geofence 60 is surrounded by additional geofences 64, all within a given cellular tower transmissions cell 65. Note that part of a neighboring geofence 64' is not fully within the cell 65, and hence, limits its benefits since a cell tower handoff by movement into cell 65' will generate a location transmission.

Geofences are implemented as software processes. Operating systems for mobile devices, such as but not limited to iOS and Android, limit the number of processes available to an application, and thus, the number of geofences is bounded. However, this limit typically exceeds the number of geofences generated using the approach described above. Therefore, additional processes are available, and hence, additional geofences are possible.

To increase the likelihood of a location transmission given movement, in embodiments of the invention, the remaining available processes implement static geofences. A static geofence is not dynamically generated given a new location as previously described. Rather, a static geofence is one that is fixed and represents those locations that are likely to be crossed by a given user. That is, users are habitual and frequent a limited set of locations often, for example but not limited to, their home, office, or favorite wine or sushi bar. By learning the frequent locations of users both individually and system wide and setting static geofences at these locations, biasing by the individual user, the probability of a location transmission is increased since additional geofences are likely crossed.

More so, these repeated locations vary by city, county, state, country, etc., as well as by other factors such as but not limited to day and time. Geographical and temporal presence can thus be used to vary the set of static geofences for a given user. For example, the set of static geofences for a given user will vary if the user is in Washington, D.C. rather than in San Francisco, Calif. Similarly, the set of static geofences for a given user will vary depending on the day and time. For example, a user frequents work on weekday mornings but frequents their favorite bagel shop on Sunday mornings and their favorite sushi bar on Thursday evenings.

Location transmissions suffer from a margin of error. Thus, it is difficult to precisely pinpoint and tag a location with a single transmission. Embodiments of this invention include automatic refining of a location of a user destination as a function of user routines, such as established by several user visits to the destination. As time progresses however, and a user frequents the same location multiple times, multiple location transmissions for the same location are recorded. In one embodiment of this invention, as representatively shown in FIG. 3, by overlapping the transmitted location along with its margin of error, a more accurate location can be derived. The overlapping of location transmissions for a given location 70 between streets 72 and within geofence 74, along with their margin of errors, represented as circles 76, yields an accurate location placement.

Figure 3:
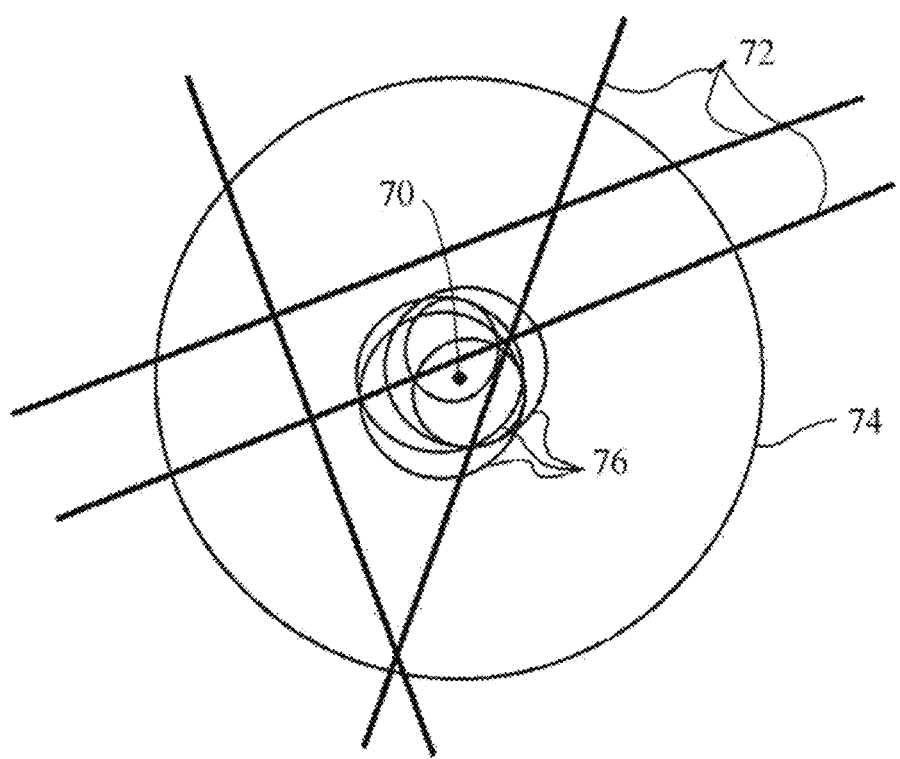
FIG. 3 illustrates the determination of a location via intersecting circles according to one embodiment of this invention.

As shown in FIG. 3, location accuracy improves as related data are collected. Related data, however, can, at times, be somewhat erroneous (in terms of accuracy). A non-limiting example is an entrance to a shopping mall. Such an entrance is not necessarily at the center of the complex. Regardless of the entrance displacement from the center of the complex, the entrance location can still be used to increase location accuracy of the mall complex since the readings for the entrance are consistent. That is, for a given user, given mobile device, given carrier, etc., such location recordings remain consistent, all be it, slightly erroneous. Thus, even dirty, namely potentially inaccurate, data can result in correct location identification.

Additionally, having established a location, corresponding lat-long pair coordinates can be reversed engineered, namely mapped back onto, a place name. These derived lat-long pair coordinates become yet an additional information component that is used by a learning system to better refine a mapping to a named place. Machine learning, data mining, and statistical approaches that are supervised, semi-supervised, or unsupervised can be used, as known in the art, to cross-correlate all available location related data.

Once determined, the user information including the location and/or the user activities are automatically stored in a database. Embodiments of this invention include a computer server for providing and implementing the tracking and/or social networking service of this invention. The computer server includes a location module to determine the user location and/or a tagging module configured to correlate manually entered user information to a user destination and a database module configured to store user information including user locations and user activities at the user locations. For social media sharing, the server further desirably includes a communication module configured to automatically share a user activity in the social networking service upon further user arrivals at a corresponding one of the user or community locations. The server can also include an association module configured to associate the user activity with the corresponding user location.

Since location transmissions are needed during movement, the obvious question arises: when should the transmissions cease? That is, the system must determine when the user has arrived at a location to know when to perform the automatic steps discussed above. As discussed above, GPS systems are an energy drain on a mobile device, particularly as the GPS remains on and linked with the satellites to maintain location detection. Keeping a GPS application operating is a drain on both the processor and the battery of the mobile device. This invention provides a method and executable application that conserves energy by not continually running during use of the mobile device.

Embodiments of this invention provide an automated method of tracking a mobile user that includes providing a location module configured to receive location transmissions, placing the location module into a sleep mode, awakening the location module upon receipt of a location transmission, and determining a location with the location module. These placing, awakening, and determining steps are repeated, thereby placing the application into a sleep mode when not needed, thereby reducing the drain on the mobile device. The application goes into sleep mode when necessary or when desired, such as when the application is not needed, e.g., during extended movement or upon an arrival at a location. In embodiments of this invention, the application can go into sleep mode whenever a time since the device awakening exceeds a predetermined time allocation, or upon a determined rate of travel exceeding a predetermined threshold, thereby indicating extended travel.

Figure 4:
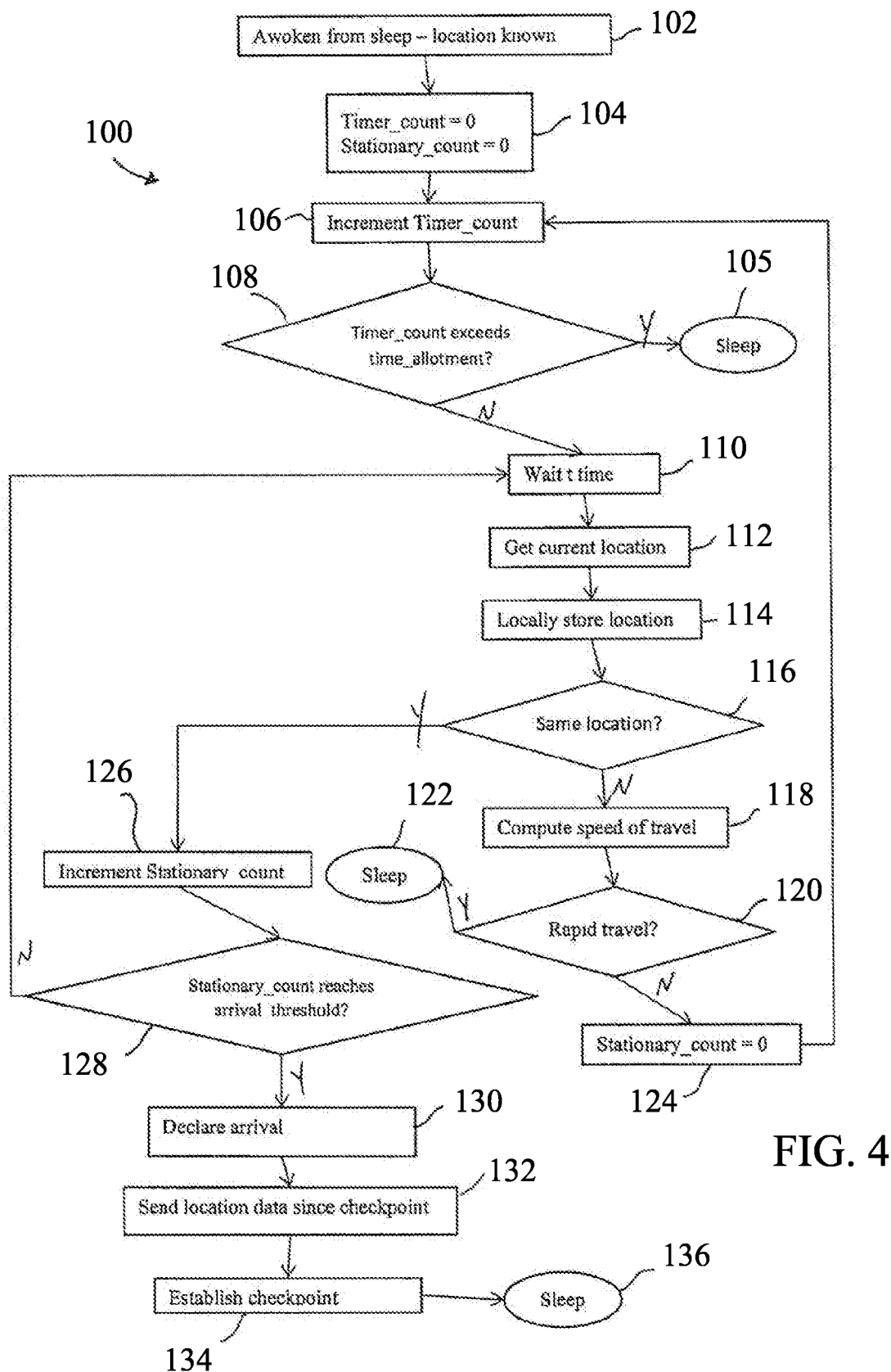
FIG. 4 illustrates the processing flow employed to identify an arrival according to one embodiment of this invention.

FIG. 4 illustrates one exemplary, and non-limiting, method according to an embodiment of this invention to automatically detect arrival at a destination. The method is useful for tracking a user's location for any of various reasons, including, for example, monitoring community members, such as for triggering events, for safety, to provide automated reminders, and/or to provide automated suggestions to the user based upon the destination and/or surrounding area. The method of FIG. 4 is particularly useful for implementing the method and system discussed above, and can be used to implement other applications and method to provide energy savings compared to GPS location methods in mobile devices.

FIG. 4 includes a flow chart 100 that includes and/or represents three distinct situations, namely, an actual arrival, rapid movement, and sporadic movement without an actual arrival. Initially, the application is in sleep mode. Sleep mode is a state when no processing, and hence no energy consumption, takes place. Processing occurs once the application is awoken. A location transmission, such as a cell tower transmission or another application obtaining location information, awakens the application in step 102. Since the application awakening occurs due to a location transmission, the current location is known.

Once awakened, the application typically has a maximum amount of time to complete its processing. This limit, called time allotment, is set by the device operating system. All processing must complete prior to exceeding the time allotment. Ideally, the application should relinquish the processing flag back to the device operating system before the operating system forcefully removes the application from its active queue. Voluntarily terminating an application, namely returning it to the sleep mode, rather than having it forcefully terminated by the host operating system, is consider good citizenship. In step 104, the application initializes two timers, namely, a timer count representing the duration of time the process has executed since last awakening, and a stationary count representing the duration of time since the last detected device movement.

As time progresses and the process executes, the timer count is incremented in step 106. In one embodiment of this invention, whenever the application processing time exceeds the operating system time allocation (108—YES branch), the application is voluntarily placed in sleep mode 105. Note that the time allocation threshold is not necessary, but set to support good citizenship.

Assuming that the time limit has not been reached (108—NO branch), the application waits for t time units in step 110. After waiting t time units, new current location data are obtained is step 112 and stored locally on the device in step 114. In step 116, the current location is compared to the previously known location. If the two locations differ (116—NO branch), the rate of travel is computed in 118. If the rate of travel exceeds a threshold (120—YES branch), the process is desirably and voluntarily placed in sleep mode 122. Rapid travel is unlikely to result in an immediate or near term arrival; thus, checking locations while moving rapidly unnecessarily uses device energy. Eventually, the application process is awoken with the device moving at a slower rate. At that time, location checking is needed as an arrival might soon occur. If or when the rate of travel is slow (120—NO branch), movement is noted in step 124, and the loop is repeated commencing with the indication that additional processing time has elapsed in step 106.

Thus far, the arrival detection process has been voluntarily placed in sleep mode either due to having exceeded the self-imposed processing allotment quota which is desirably set just slightly below the operating system's time limit that leads to the removal of the application from the active queue (108—YES branch) or having travelled too rapidly (120—YES branch). Slow travel has resulted in simply recording the locations traveled, noting the movement exists in step 124, and awaiting either arrival or process termination.

Arrival is determined when the same location is detected for a sufficient duration of time. That is, an arrival is potentially determined when the location remains the same (116—YES branch). The stationary detection count is then incremented in step 126. If the stationary threshold is not yet exceeded (128—NO branch), the application waits for t time units in step 110, and the current location is obtained in step 112 and stored locally in step 114. A sufficient and predetermined duration at the same location eventually surpass the arrival detection threshold (128—YES Branch).

Once arrival is determined, arrival is declared in step 130, all data regarding the prior locations visited and stored locally are compressed and sent to the back end system supporting the application in step 132. A new location checkpoint is established in step 134, and the process is placed in sleep mode 136. From the sleep modes, the process of FIG. 4 repeats upon a known location.

Compression of location data is typically performed prior to local device to back-end system transmission as often the location data many not be needed at the back end. Location data may not be needed in cases, for example but not limited, during rapid travel. Although exemplified as having data compression occur prior to the sending of the data to the back-end, it is within the scope of this invention to compress location data prior to storing them locally.

All parameters described above for FIG. 4, for example t (for the time units), timer count, etc., are system and device dependent. Experimentation with and fine tuning of these and other parameters is within the scope of this invention. Also within the scope of this invention is the tuning of these and other parameters via the use of machine learning, data mining, and statistical approaches; supervised, semi-supervised, and unsupervised approaches can be used.

As discussed above, once the user has arrived at a destination, the location identification, user activities at the location, and/or any proximate third party members of the user's community are determined, if not already known. In this way, the devices automatically continually determine locations which can be used to identify any establishments and/or any community members at or within proximity to the location.

User activities are actions or events. Example user activities include but are not limited to "drinking wine," "flying," "reading," "attending conference," or "commuting." Users specify a particular user activity either by selecting from a provided list or by entering a different user activity. As discussed above, the provided list is generated by storing all previously entered user activities from all systems users but biasing the ranking of the provided activities based on context, the local user, their community, or a combination thereof.

All location and user activity pairs are stored in a database correlating the location with the activity. Any of the many database management systems or storage schemes known in the art can serve as the platform for this location-activity database. Furthermore, it is well understood in the art that the location-activity database can store many additional features. For example, the user identity and date and time of the pair are recorded.

Over time, the database grows and contains a sufficient number of pairs to support mining. The volume of data needed to mine correlations is dependent on the mining algorithm deployed and the level of accuracy needed. As known in the art, there are many machine learning, data mining, and statistical approaches to support mining. By using any of the many available such approaches, either individually or in combination, a local user activity preference per location is learned. Example learning approaches include supervised, semi-supervised, and unsupervised approaches including but not limited to Naïve Bayes, Neural Networks, Support Vector Machine, and Associating Mining based techniques. The use of proprietary mining techniques is likewise within the scope of this invention. Once local user preference is learned, this preference is used to bias the aforementioned provided user activity list.

There are many approaches to identify locations. Automated location identification is accomplished by periodic checking of the current location. Periodicity of checking depends on, for example, the method used to determine the location, the desired frequency of reporting, recording, and notification, and the resources available to support the checking. Other periodicity determination approaches known in the art can likewise be used. One approach to automate location identification is the periodic determination of lat-long pairs via the use of a GPS device. An online service or a locally resident database can be used to correlate the GPS readings with locations. A preferred embodiment of this invention uses the aforementioned location database. Whenever a transmission to a connected cell tower is made, the cell coordinates of the transmitting device are used as a search query against the location database. If a match is detected, that location is identified. Another preferred embodiment detects locations upon the crossing of geofence boundaries as previously discussed. Note that both dynamically determined geofence boundaries and static geofence boundaries detect a location. Yet another preferred embodiment detects locations by capitalizing on location transmissions generated by any other application operating on the mobile device requesting location information.

In embodiments of this invention, local users, unless disabled by a local user, can be provided with automated notifications for themselves and for their community members. These notifications describe locations, activities, or correlated locations and activities for themselves and their community members. For example, unless disabled by the user, any time a user arrives at a new location, the local user and their communities can be notified of the user's new location. Automated location detection and notification, unless disabled, occurs without requiring a local user prompt.

Similarly, activity notification can be automated. Once a user arrives at a location, a set of activities previously occurring at that location is shared with the community or provided to the local user for information or sharing. If the user chooses to confirm at least one of these past activities, both the local user and their respective community members are notified of this at least one activity.

In another embodiment of this invention, automated notification involves shared experiences. A shared experience is one that associates multiple users. These associations can be passive or active. A passive association is strictly informative in nature while an active association requests an action. Non-limiting examples of passive shared experiences based on locations include: "User A is at User A's office, as is User B" and "User A is at home as is User C." Note that the first example involves multiple users at the same physical location, namely User A's office, while the second example involves multiple users at the same relative locations, namely their homes, but at different physical locations.

Similarly, passive shared experience notifications can be based on user activity. Non-limiting examples of passive shared experiences based on activity include: "User A is eating lunch as is User B" and "User A is participating in her favorite sport as is User B." Note that the first example involves multiple users participating in the same activity, namely eating lunch, while the second example involves multiple users involved in similar nature of activities, namely participating in their own favorite sport, which can be different actual activities, namely racquetball and swimming. In both passive shared experiences based on location and on activity, known in the art machine learning, data mining, and statistical approaches that are supervised, semi-supervised, or unsupervised approaches can be used to correlate relative locations and activities to physical locations and activities.

Other shared experiences can prompt for action, and are thus considered active. A non-limiting example of an active shared experience prompting for action includes: "User A posted a picture when at Penn Station; you are now at Penn Station; please post a better picture?" Thus, active shared experiences request the user to actively react. As above, active shared experiences can be location or activity based and can be absolute or relative. Note that it is likewise within the scope of this invention that individual user notifications be active and passive, in a similar manner as described above. However, the correlation of locations and activities both for passive and active are based strictly on the current, past, or projected expected activities of the individual user rather than those of multiple users.

Typically, only changed locations and activities are notified. That is, a location or activity is not typically repeatedly identified. However, a local user can request repetitive notifications based on any triggering condition known in the art.

Local users do not always remember to indicate a new location name or confirm which of the possible suggested name or names the system indicated for the given the location. As such, it is at times advantageous to prompt the local user for information. However, overly aggressive prompting might annoy the user. In embodiments of this invention, the application non-invasively prompts the user upon detecting an unknown location for the given local user. To avoid annoyance, prompting is repeated only rarely, say twice; the number of repeated prompts can be set as a parameter. Similarly, to provide a sense of comfort, if the back-end system recognizes the location based on the local user's community members' naming schemes, it prompts the local user with guiding messages, for example but not limited to "Many of your community members call this location The Tasting Room".

Identification of activities associated with a given location or a given community member can be additionally or alternatively automatically inferred in multiple ways. In embodiments of this invention, the computer system can automatically determine a positional destination of a user, such as by using a mobile device discussed herein, and automatically deduce as user information a location type and/or user activity of the positional destination. The user information can be deduced, at least in part, based upon the destination context. Exemplary context information includes, without limitation, time-dependent information (e.g., what time of day is it?), community information (e.g., who is also there?), and/or third-party information about the positional destination. This method, tied with automatic sharing of the user information in a social networking service, can provide a partially or fully automated process for determining user location and activity.

In one embodiment of this invention, the automatic deducing of the user information is based upon known or learned user routine. As discussed above, local users typically follow standard routines. Some routines are daily, weekly, monthly, etc. Other routines are context dependent. Regardless of the nature of the routine, learning via any of the many statistical, machine learning, data mining, or business analytical techniques known in the art, enables predictive behavior and automated activity and location suggestion. For example, but not limited to, if a local user always goes out to lunch at noon on every weekday, then if an unknown location is detected on a Tuesday at noon, then the application can suggest that this unknown location is likely a restaurant and the activity is likely eating lunch. Similarly, routine identification enables the prevention of transmissions both positional and informational. For example, but not limited to, if a local user always goes to sleep at midnight on Sunday through Thursday and awakens at 7:00 am the following day, then energy can be saved if the application voluntarily places itself in sleep mode during the hours that the local user is known to be sleeping. Additionally, routines can involve a sequence of activities and locations. A non-limiting example of a sequence of activities includes: On weekdays, Eric arrives at his office at 8:00 am, drinks coffee at 10:00, develops software from 11:00 am until 5:00 pm, commutes home at 5:30, and finally, arrives at home at 6:00 pm.

Another location and/or activity deduction approach is by association. The automated deducing can include automatically associating a user with a second user at a positional destination. If the second user's location and/or second user's activity is known, then the system can automatically infer the location type and/or user activity of the first user from the second user location and/or activity. Consider a previous known event such as: "Community member Sally swimming at the Somerset pool", assuming that the Somerset pool location was previously identified. As an example of automatically determining a current activity of community user Sam, the system identifies through location determination that Sam is currently at the same location as Sally, and also that Sally is currently at the Somerset pool. From this information, possible automatically postulated associations and activities are: "Sam is at the Somerset pool", "Sally is swimming", and "Sam is swimming". Thus, it is possible to infer an activity for a community member from association with another community member. It is within the scope of this invention to use any logical inference methods known in the art to generate plausible associations. It is also within the scope of this invention to obtain confirmation of the plausible postulated activity by the community member, in this case Sam, by asking either Sam or Sally or by any other means known in the art.

Desirably the computer system operating the MPSM automatically stores past user information, including past location type and/or user activity of the positional destinations of all users. User information for future visits to repeat positional destinations can be automatically deduced as a function of the stored past location type and/or user activity of the positional destination. In embodiments of this invention, the system can rely on recorded previous activities of a user, a community member, or any system user at a given location to postulate on a user's activity at a given location. Past context information for past visits to the positional destination by the user and/or community members of the user can be compared to a current context of the user's visit to the positional destination to deduce the user information. In one embodiment, the system can reduce possible location types and/or user activities as a function of the past location type and/or user activity of the positional destination.

As an example, at a given Location A, users previously studied, talked, ate, and drank. Thus, if a user's positional destination is detected as at Location A, then plausible activities postulated can be studying, talking, eating, and drinking. More so, if the given user's community members only previously talked, ate, and drank, it is with a higher probability to postulate that the given user is talking, eating, and drinking rather than studying. Furthermore, if the given user visited Location A previously, but only talked and drank, then an even higher probability is that the user is currently talking and drinking rather than eating and studying. It is within the scope of this invention to postulate some or all of the previously detected activities of a given location. More so, it is within the scope of this invention to rank order the activity suggestions according to the relevance of the previously visiting users to the given current user. As previously described, the system can request confirmation of suggested activities through the user's mobile device.

The system can additionally or alternatively reduce possible location types and/or user activities as a function of the past location type and/or user activity of the positional destination as a function of the time of day. The system can rank possible location types and/or user activities of the positional destination based upon known past time periods corresponding to the time of day of the current user visit. For example, again given Location A, if previous visiting users were recorded to study one or more times during the intervals: 3:00-4:30 PM and 7:30-9:00 PM, and to drink one or more times during the intervals: 4:00-7:00 PM and 8:30 PM-2:00 AM, then a current visiting user at Location A at 3:15 PM is likely studying, at 4:15 PM is likely to be either studying or drinking, and at 1:00 AM is likely to be drinking. More so, if the given user's community members only studied between 3:15-4:30 PM then it is with a higher probability to postulate that the given user is studying rather than drinking at 4:15 PM. Furthermore, if the given user visited Location A previously but only studied, then an even higher probability is that the user when at Location A is studying. It is within the scope of this invention to postulate some or all of the previously detected activities of a given location. More so, it is within the scope of this invention to rank order the activity suggestions according to the relevance of the previously visiting users to the given current user. As previously described, the system can request confirmation of suggested activities through the user's mobile device.

In embodiments of this invention, time context alone can be used to postulate activities. For example, if most days, a user is recorded to be drinking coffee between 9:00-10:00 AM, then, without contradictory information, a plausible activity postulate is that at 9:35, the user's activity is drinking coffee. Again, as previously disclosed, it is within the scope of this invention to rank order the postulated activity suggestions according to the relevance of the previous users to the given current user and/or to obtain confirmation of suggested activities.

Additionally, it is also within the scope of this invention to rank order the time postulates based on frequency of occurrence within the time interval. This rank ordering applies to both location based and location independent time based postulates. For example, if in the interval 4:00-4:30 PM, community members studied 25 times but drank 5 times then, at 4:15, it is with a higher probability to postulate that the given user is studying rather than drinking.

In embodiments of this invention, the system can search and/or use, if available, external, third party information about the positional destination for postulating activities for a given location. For example, third party vendors might provide, either free of charge or for a fee, activity information for a given site. Consider a marketing website of a centralized homepage for a grocery store chain. Such websites are likely to contain addresses of many or all of the associated stores. Since these stores all support shopping, an activity associated with these locations is shopping. Similar information can be derived or purchased from other sources such as but not limited to commercial information repositories. Additionally, maps can be parsed. Given a location of a road, an activity of that location is likely to be driving. Various and alternative third party information gathering approaches and their incorporation into activity classification and postulation can be incorporated into the method and system of this invention.

Suggested activity information, particularly but not limited to information obtained or derived from third party vendors, might be additive or might be contradictory. Thus, combining or reconciling potential activities is needed. The use of voting schemes, biased based on credibility of the source or on frequency, such as majority, or other known techniques, can be incorporated in the method and system of this invention. Note that differing suggested plausible activities may additive or may be contradictory. The use of techniques such as, but not limited to, conflict resolution methods, ontology determination, and clustering, etc., can be incorporated to recognize potential conflicts and to expand classification is within the scope of this invention.

Additionally, the classification of plausible activities based on activities occurring in the surrounding vicinity is likewise within the scope of this invention. For example, consider an unknown location adjacent to two known locations, such as, but not limited to, two neighboring stores or two neighboring beaches. For the neighboring stores, known activities might include shopping and strolling, while for the neighboring beaches, known activities might include sunbathing and swimming. Given location proximity, it is within the scope of this invention to suggest a user's activity at the unknown location to be either shopping and strolling or sunbathing and swimming, respectively. Confirmation can always be obtained for suggested activities and to bias suggested activities based on user familiarity and frequency of occurrence.

In embodiments of this invention, local users can opt to delay their notifications. That is, once a location is visited or an activity occurs, a local user can opt to have the notification of the location or activity be delayed by some period of time. Delaying a notification provides the local user with the ability to notify their community of the location visit or activity occurrence, but still provides the local user time to progress to the next location or activity.

Notifications can be complemented with correlations with other community members. That is, both the local user and their respective community can be automatically notified with a comparison. A comparison, for example but not limited to, can identify other community members having previously conducted a specific activity or having visited a given location previously. Comparisons are made by checking other community member locations and activities against those of the local user. Checking is performed via a search of the location-activity database. If a match exists within a specified or predetermined period of time, a comparison notification is made automatically. The period of time can be arbitrarily set or can follow some logical time quantum such as hour, day, week, etc.

Locations and activities are known by name. However, in addition to a name, locations and activities can have associated personal labels. Labeling locations and activities can detail familiarity to the location and activity. User labels for locations can be surrogate names, for example, "favorite city" for Chicago, can be songs or sound waves, for example song words "my kind of town, Chicago is" for Chicago, can be a picture, for example "the Water Tower" for Chicago, can be a video, for example "a panoramic view of the Chicago skyline" for Chicago, or any combination of these and other multimedia tags supported by the local device. Similarly, user labels can exist for activities. For example, "favorite vice" for drinking wine, or it can be a song or sound wave, for example the song words "a bottle of red" for drinking wine, or it can be a picture, for example, a wine bottle picture for drinking wine, or it can be a video, for example "a panoramic view of a vineyard" for drinking wine, or any combination of these and other multimedia tagging labels supported by the local device.

In embodiments of this invention, local users and community members can comment on their own and each other's locations and activities. Comments can take any of the many multimedia forms provided by the local device. These include, but are not limited to, text, sound, pictures, videos, or any combination thereof. Multiple comments can be made by the local user, their community, or combination thereof. In addition to stating their opinions (commenting), community members can prompt for clarification. That is, by issuing "what" comments, community members request additional information on the posted locations and activities. Additionally, user can "like" their own and each other's locations and activities. By "liking" a location or activity, community members express their satisfaction of their respective community members' presence in terms of location and activity. Multiple community members as well as the local user can "like" a location and activity.

The method and systems of this invention can track vast data on both the local user and their respective community members. These data cover, including but not limited to, locations, activities, and also individuals both who are system users and those who are not. These data can be stored and summarized. A summary of the local user and community member locations, activities, time durations involved in each of these locations and activities, individuals who they encountered, etc., can be computed and presented to the user. This summarization can range from simple statistical aggregation to advanced correlations as derived by any of the many, both individually and combined, machine learning, data mining, business analytics, and statistical techniques known in the art.

Information that can be aggregated or derived can answer, exemplary but not limiting, questions such as: how much time a local user spent doing things, such as, working at home, working out, walking the dog, commuting to work?; how much time a particular community member spent doing things, such as, working at home, working out, walking the dog, commuting to work? (Note that the information derived for the community member is based strictly on the information that that particular community member chose to share.); who are the five most common individuals that a particular user interacts with?; what is the likelihood that after seeing a particular user, the given local user would see a particular different individual?; which activities and locations are most closely associated with each other and when are they most likely to occur?; which three users among a given community are most likely to visit a particular location together?

Local users can be provided with summaries of their locations, durations at these locations, and activities at these locations. Furthermore, at the discretion of the local user, these summaries are made available to their community members.

The system can also generate and maintain both aggregation and derived information. This information can be used to optimize suggestions to avoid obstacles, for example, but not limited to preferred routing of commuting path, promoted target advertising, for example but not limited to location of nearby ice cream store for those users who frequently record "eating ice cream" as an activity, and a host of other informational services known in the art.

The following examples illustrate, without limitation, the above discussed data capturing, storing, analyzing, mining, and presenting MPSM functionalities of this invention. It is to be understood that all changes that come within the spirit of the invention are desired to be protected and thus the invention is not to be construed as limited by these examples.

FIG. 5 illustrates a location summary of an individual user. As shown, two boxes are presented. The top box is a summary of where and how a user spent their last two weekend days, while the bottom box provides a summary of where and how a user spent their last five weekday days. As shown, in both cases, the duration of time spent in a given location is listed. For example, looking at the top window, the user spent about 9 hours in Georgetown in Washington and about 1 hour in O'Hare in Chicago during the last two weekend days. The user was obviously on travel as the user spent less than a minute at home during the weekend.

FIG. 6 illustrates a user's transit summary, which is a summary of the user's transit characterized by speed, namely slow, medium, and fast travel, and when, where, and for how long did this travel occur, namely, duration and initial and terminating locations. The average speed is likewise noted. For example, the user traveled fast from Denver airport to home, a distance of 964.57 miles at an average speed of 291.29 MPH, and it took roughly 3 hours.

FIG. 7 illustrates a user's own activity summary. That is, a summary of the user's weekly activity is provided that includes the frequency of and percentage and absolute time involved in the activity over the past week. For example, the user was at the Four Seasons twice within the week for 3.4% of their reported time or about 4 hours.

FIG. 8 illustrates a user's time summary in comparison to their friends. The summary of the user's time breakdown is made in comparison to others within their community. For example, the percentage of time the user spent at home as compared to that of their friends is roughly 14% (0.14$x$) versus in transit which is 1.53 times as much.

FIG. 9 illustrates a summary of a user's activities shared with others. The summary of the user's activities is shown providing an indication of the amount of time and activities jointly experienced. For example, the user jointly had sushi with and visited Ophir at his home. Also indicated in the bottom portion of the frame are the names of one's community members that the user did not see (top listing) or interacted with (bottom listing) in the past week.

Figure 11:
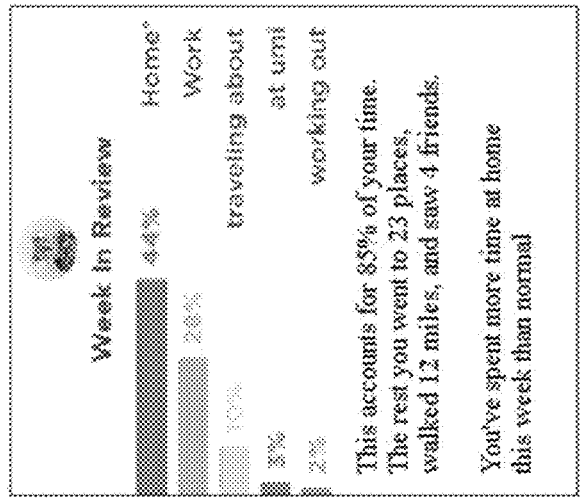
FIG. 11 illustrates a view presented to users summarizing their weekly behavior according to one embodiment of this invention.
Figure 10:
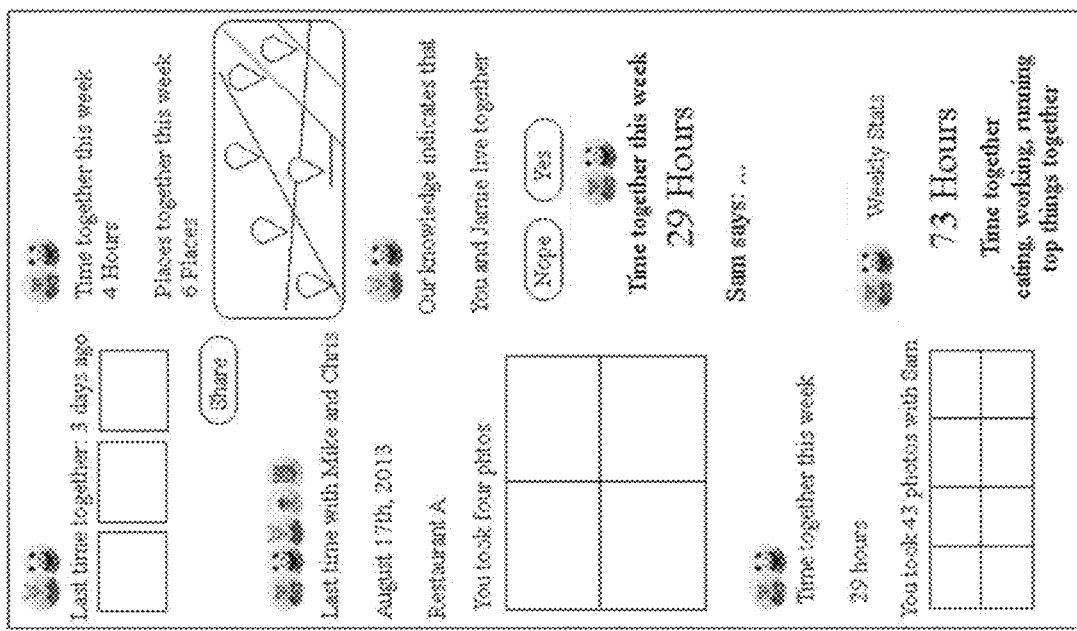
FIG. 10 illustrates a view presented to users that quantifies their shared patterns according to one embodiment of this invention.

FIGS. 10 and 11 illustrate views presented to the user of a quantified together board and of a quantified individual board, respectively. FIGS. 10 and 11 represent information in a more pleasing form for presenting to the user. FIG. 10 summarizes time spent and activities experienced together. For example, two users spent 73 hours together this week eating, working, and running. The last time they had drinks together was two weeks ago (bottom right boxes). The last time they were together was 3 days ago (top left box). FIG. 11 summarizes a user's week in review. The week in review highlights the main activities and locations (top half). Likewise summarized are other behavior patterns including anomalies (bottom half).

Embodiments of this invention incorporate picture characters or pictograms into the mobile positional social media domain. The method and system of this invention allow users to define, develop, incorporate, modify, classify, and/or transmit pictograms, such as representing user locations and/or activities, to community members and to global users. In one embodiment, a user of a MPSM device can select or create new one or more pictograms specific to themselves, to their community, or globally, that is, to any user that has access to that one or many particular pictograms. Users can define or redefine existing meanings of each pictogram; a user can incorporate existing, namely already created and defined pictogram, into their messages; a user can associate a picture to a given pictogram; a user can modify existing pictograms both for local and for her/his community; and/or a user can also classify a pictogram as to its type, for example, but not limited to, mood, activity, location, etc.

Any suitable pictogram can be added and/or used in the method and system of this invention. One exemplary pictogram is known as Emoji. Emoji is a commonly used term that generally means picture characters or pictogram. Some Emoji representations are mapped onto Unicode representation and are thus available for use in a variety of desktop and mobile device applications including the invention disclosed herein.

Using the location and/or activity determination methods discussed herein, the MPSM can determine, and possibly announce, activities occurring, having occurred, or are scheduled or likely to occur using pictograms. The pictograms can also be used to associate activities with a given location; the location of interest either being, will be, or was previously visited by a community member or is of relevance to a user request.

In one embodiment of this invention, a method and system of sharing locations and/or activities of a user participating in a MPSM includes the system receiving a user-defined pictogram for a destination and automatically associating the pictogram with the destination. The method desirably also includes the automatic sharing of the pictogram in the social networking service upon further user arrivals at the destination prior to receiving any additional user information. The pictogram desirably corresponds to a user activity at the destination, and can be manually selected by the user from a list of predetermined pictograms or other photos or drawings, etc.

Embodiments of this invention include a system that learns to associate the pictogram with the destination upon further visits. The pictogram can be automatically presented to the user through a mobile device upon reaching the destination for confirmation and/or changing to or selecting a new pictogram. These steps can occur for several visits to the destination, with the goal for automated learning and ultimately to provide an automated sharing of the pictogram for the destination. Where several pictograms have been associated with a destination, the several pictograms can be presented over time for confirmation, preferably in a ranked list. In addition, the method and system can automatically determining one or more of the plurality of pictograms to share at a further arrival at the destinations as a function of an automatically determined context of the further arrival, such as based upon a time of day or the presence of fellow community members also at the destination, as discussed further herein.

Figure 12:
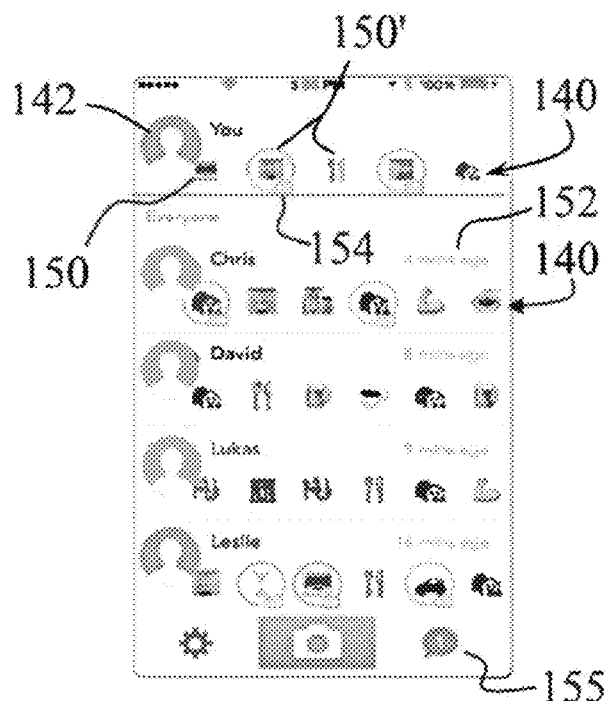
FIG. 12 illustrates a view presented to a user of his and his community's activities in a pictogram format, according to one embodiment of this invention.

The pictograms according to this invention allow for efficient pictogram summaries of user and community activities and/or locations for any predetermined time period, such as a day, week, month, and/or year. FIG. 12 is a mobile device GUI that shows users' timelines of activities via pictograms. The pictogram timeline 140 includes pictograms that provide visualizations of a person's and their community's daily activities. The user activities are visually compared to what others are doing. The user and the community are represented by photographs and their names. The most recent activity is represented by a pictogram 150 on the horizontal timeline 140 that is closest to the user pictogram 142. The remaining pictograms 150' for each user are showing in order of newest to oldest. The timeline can also display the timing 152 of the most recent pictogram. Feedback by others on the user's activity is also provided. In FIG. 12, one comment is currently available, as shown by the comment notification 155.

In embodiments of this invention, photographs or other data can be associated with the pictograms. In FIG. 12, a camera icon 154 can be associated with, such as by overlapping, any pictogram to show when one or more photographs or other data items are associated with the pictogram. Community users can touch or click the pictogram to display the associated photograph. The camera icon at the bottom of the screen can be used by the user to associate or change photos.

In another embodiment of this invention, users can be grouped by common current or latest activity. As shown in FIG. 12, the first two community members display the same 'house' pictogram, indicating a common activity, albeit not necessarily at the same location (i.e., each is that their own home).

Figure 13:
FIGS. 13-15 illustrate various pictogram summaries for user activities.
Figure 14:
Figure 15:
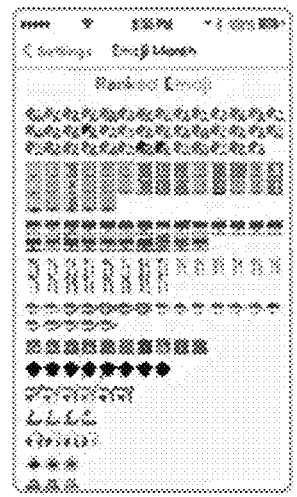

FIGS. 13-15 illustrate alternative pictogram summaries of a user's locations and/or activities. FIG. 13 illustrates a summary of a user's daily activities via pictograms. The visualization summary shows the individual's activities by pictogram for several days. FIG. 14 illustrates a pictogram summary of a user's activities on a month-by-month basis. FIG. 15 illustrates a histogram summary of a user's monthly activities aggregated by type and presented as a visualization of an individual's monthly activities.

In embodiments of this invention, pictures can be associated with the pictograms. Additionally, it is possible to annotate the image with text using an annotating tool at the bottom of the GUI. To assist the user, the system may show or suggest a pictogram representation. The selection of a new pictogram is possible if desired or if the system suggestion is incorrect.

The invention includes a method of determining medical conditions of users participating in a social networking service using the above described monitoring and learning method and system. From the automated monitoring of destinations and user activities described above, the computer system learns activity patterns for users. In embodiments of this invention, deviations in activity patterns can be determined and analyzed for possible indicators of health concerns.

As an example, it is generally known that deviation from daily behavioral patterns is a potential warning signal for depression. Signs and symptoms of depression include the loss of interests in daily activities, appetite or weight changes, and sleep changes. That is, an individual might no longer have interest to participate in former hobbies or social activities. The individual may exhibit a change in eating habits causing weight gain or loss. Additionally, the individual may suffer from insomnia resulting in excessive walking in the early morning hours, or to the contrary, hypersomnia resulting is reduced activity. All of these changes in behavioral patterns can be automatically detected by location and activity aware MPSM technology of this invention.

Using the automatically learned behavior in terms of the locality of a user using MPSM technology, a sudden change in locality patterns of an individual both in terms of locations visited and movement patterns, can indicate a potential early onset of depression. That is, if the individual previously seldom, if ever, walked in the morning, and now, walks regularly in the early hours, this might be a cause for alarm. Such deviation in activity is detected, analyzed, and correlated to depression or other related condition using an inference engine using any of the many well-known in the art pattern detection algorithms that are part of an MPSM system according to this invention. Additionally, if the individual often visited a gym, regularly attended movies at a local theater, often stopped off at a neighborhood ale house after work, etc. and suddenly fails to visit any of those locations, this too might be an indicator of possible depression. Again, all of these deviations are automatically detected via the MPSM technology described herein.

Deviation from automatically learned activities and gatherings can be used to trigger concerns. These too are automatically detected via the MPSM technology according to this invention. Consider an individual user who although continues with the same locational patterns, deviates significantly from their automatically learned activity patterns. For example, while an individual may continue to regularly go to their office, their time of arrival and duration of stay at their office might change suddenly. Additionally, while at their office, they might have previously, regularly eaten lunch with several of their community members and had often taken a coffee break with other community members; if these social meetings suddenly cease to occur, this too can be a cause of potential concern and is likewise automatically detected via MPSM technology according to this invention in the manners previously described.

Additionally, eating patterns might vary. If a user frequents an eating establishment often, at a far greater rate than previously, this condition is detectable by MPSM technology of this invention and might be a cause for alarm. More so, given precise accuracy, even relatively frequent or infrequent positioning within one's kitchen might indicate excessive or reduced eating behavior, respectively. Again, such behavior is automatically detected via the method and system described herein.

As will be appreciated, not every deviation from activity patterns means depression, as the user may have a reason for the deviation, such as being on vacation or having a broken leg. Embodiments of this invention include automated analysis of detected deviations to determine the significance of the deviation, such as using the inference engine, and can consider any other user information, before correlating the deviation to a possible medical condition. As discussed above, the changes in behavior may be tied to a location, such as no longer eating with coworkers despite being at work. If the system detects the user is in Maui instead of at work in Chicago, then not eating with coworkers likely is temporary, and not of concern. Likewise the system can identify and/or learn events in the user's life, such as from MPSM information according to this invention, and/or identifying words and/or ideas from sent or received messages (e.g., e-mail, IM, text, etc.), which may explain a deviation from normal activity, such as "broke my leg" or "tired today from having excessively celebrated last night."

As discussed above, embodiments of this invention incorporate an inference engine for analysis and/or correlation of deviations. The inference engine processes real time data feeds and combines them with historical information to arrive at fully automated decisions. These decisions take the form of determining whether or not a user is deviating from normal behavior. Note that regardless of the determination, the potential correlation is added to the user's history so that the inference engine may consider it in the future. Correlations in a user's behavioral pattern that the system has previously identified strengthen or weaken evidence when appropriate.

In embodiments of this invention, the inference engine identifies correlations by using recent methods designed for automatic correlation detection in big data or data analytic applications, such as but not limited to the maximal information coefficient. A variety of such metrics are computed and considered, so that evidence does not depend on a single metric; correlations supported by a wide variety of metrics are treated with increased confidence. The inference engine makes recommendations by considering the probability of a severe condition given the user's history and current state. These probabilities become more nuanced or refined as more data become available.

Statistical techniques, machine learning, data mining, pattern detection and/or any other analytical techniques known in the art can be incorporated as needed to learn users' behavioral patterns. This enables the system to improve performance by fine-tuning the alert recommendation criteria. The system continuously learns normal patterns of behavior for a user and learns how much the user's behavior should deviate before any alarm needs to be triggered. Behavior deviation information from a wide, potentially global, set of users is likewise evaluated to better calibrate the degree of behavioral change of the individual user that should be noted prior to sounding an alarm. It is within the scope of this invention to incorporate outside sources to better calibrate this necessary deviation level.

It is also within the scope of this invention for the automated decision to issue an alarm, to the user or another person, to be based, at least in part, on the severity of the behavioral deviation or on the level of severity of the ailment associated with the deviation pattern noted. That is, complete loss of sleep is of greater concern than the periodic missing of meals or the increase in tardiness to meetings. Severe deviations can more readily trigger alarms. Multiple deviations can more readily trigger alarms. Prolong deviations can more readily trigger alarms.

In embodiments of this invention, when an alarm is triggered, the condition or conditions triggering the alarm are identified. Also identified can be the duration of the deviation noted and the suspected ailment that might be associated with the noted deviation.

It is also within the scope of this invention to account for external factors that can cause deviation, such as, for example, without limitation, correlations between geographic locations and certain conditions. A user visiting an area with air pollution is less likely than normal to go for walks. Similarly, when visiting high altitude, activity levels might be reduced. Thus, accordingly, the degree of deviation from the normal behavior patterns needed to trigger an alarm might be changed.

In addition to detection, the disclosed invention supports the automatic notification of selected community members, specialized health practitioners, or alarm monitoring personnel or systems if deviation in behavior is detected. A set of conditions can be set that trigger a notification, as noted earlier. Either a particular community member or any other predetermined set of individuals or organizations can be notified should a condition be triggered. It is within the scope of this invention to notify different sets of individuals or organizations depending on differing behavioral changes, hence different triggering conditions.

It is also within the scope of this invention to have different sets of conditions to trigger an alarm rather than a single triggering condition. Additionally, it is also within the scope of this invention to have differing triggering conditions depending on the differing ailment symptom sets.

It is also within the scope of this invention to weigh the symptoms that are monitored and trigger the alarm differently. Symptom weighting can be based on frequency of occurrence within a given time period, severity of the indication that the symptom represents, or any of the many symptoms, or more generally features, weighting schemes known in the art.

In embodiments of the invention the notification sent can depend on user locality. For example, if the user triggering the alarm is local to Chicago, Ill., then community members notified could potentially be those residing or currently located within a given radius of Chicago. This radius of notification can be based on, without loss of generality, geographic boundaries, population density, number of community members in the vicinity, or any similar measure. Similarly, with access to the community members' calendars, those members who will potentially be near the user triggering the alarm within an upcoming period could be notified of the triggering conditions of the potential ailment. The tolerated duration of delay to be in contact with the trigger alarm user can be based on a predetermined period of time or based on the severity of the ailment under consideration.

It is also within the scope of this invention to select the notification set depending on the modified user activity. For example, if the user triggering the alarm was often hiking and now is neglecting such behavior, it is possible to alert those community members with similar or identical interests, such as hiking or walking, as these members might be good candidates to engage this particular user. Similarly, if the user triggering the alarm is related to eating, for example, community members who frequently dine out might be alerted as they can coordinate, impromptu coordinate, or serendipitously coordinate, a common dining outing to engage the user triggering the alarm.

Additionally, it is also within the scope of this invention to simply alert the user triggering the alarm of their deviation in behavior as they might not be aware of this deviation him/herself. It is also within the scope of this invention to alert the appropriate health practitioners or family members interested in or monitoring the well-being of the particular user triggering the alarm.

FIGS. 16-24 graphically or otherwise illustrate a simple, exemplary determination of activity patterns and deviations, according to embodiments of this invention. Although most of the figures illustrate the monitoring of the top, or most frequent, activities, localities, and interactions of the user's activity pattern, it is also within the scope of this invention to monitor any number of any community member interactions, activities, or localities.

Figures 16, 17:
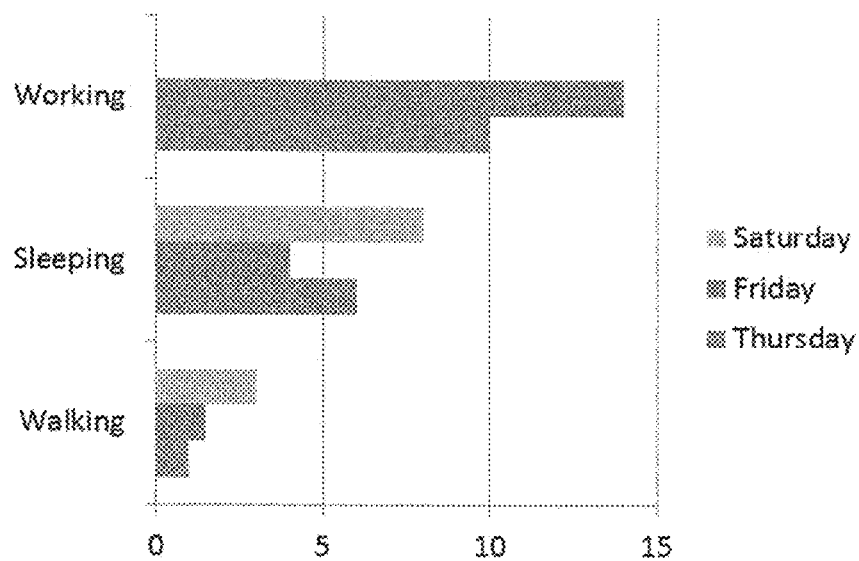
FIG. 16 illustrates an exemplary summary of top activities determined according to embodiments of this invention.
FIG. 17 illustrates an exemplary summary of selected activities across multiple periods according to embodiments of this invention.

FIG. 16 illustrates an exemplary summary of top activities determined for a user according to one embodiment of this invention. For each top activity listed, the corresponding total duration spent on that activity over the covered time period is indicated. The number of top activities and the period of activity covered are parameters that can be adjusted. As shown in FIG. 16, the top activities determined for the user during the exemplary duration were: working, sleeping, walking, eating, and reading along, with the corresponding total time for each spent over a 48 hour period. Specific period ranges can be selected elsewhere. The activity granularity corresponds to those activities learned and detected.

FIG. 17 illustrates an exemplary summary of selected activities across multiple periods. For each of the three activities listed (working, sleeping, and walking), the total duration spent on the activity in each of the three days (Thursday, Friday, and Saturday) covered is indicated. As shown, the analyzed community member did not work at all on Saturday, but slept significantly more than s/he had on Friday. The granularity of the period was set at 24-hours. Periods can be set at any granularity including but not limited to hours, days, weeks or months. Parameters indicating the period length, number of periods covered, and number of activities are set elsewhere; default parameters can also exist.

Figures 18, 19:
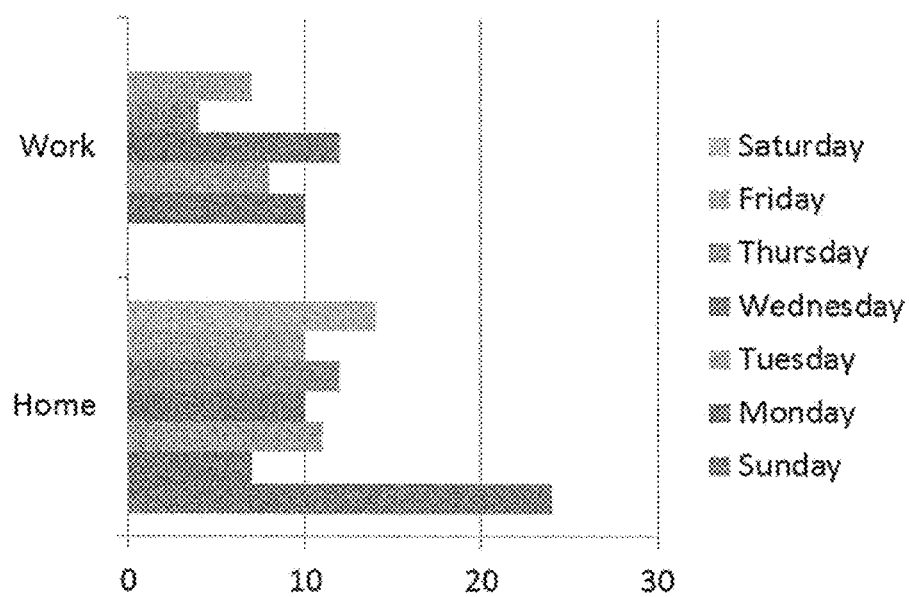
FIG. 18 illustrates an exemplary summary of top localities determined according to embodiments of this invention.
FIG. 19 illustrates an exemplary summary of selected locality across multiple periods determined according to embodiments of this invention.

FIG. 18 illustrates an exemplary summary of top locations determined for a user. For each top locality listed, the corresponding total duration spent at that locality over the covered time period is indicated. The number of top localities and the period of activity covered are parameters that can be adjusted. Default parameters exist. As seen, the top localities were: Chevy Chase, Md.; Washington, D.C.; Potomac, Md.; Bethesda, Md.; and Rockville, Md. along with their corresponding total time spent at each of these locations over a 24 hour period. Specific period ranges are selected elsewhere. The locality granularity corresponds to those localities learned and detected. This includes geographic locations as shown as well as relative locations, such as home or work (not illustrated in FIG. 18, but illustrated in FIG. 19).

FIG. 19 illustrates an exemplary summary of selected localities across multiple periods. For each of the two relative locations listed (home and work), the total duration spent at that location in each of the seven days (Sunday through Saturday) covered is indicated. As shown, the analyzed community member was absent from the work location both Saturday and Sunday; in contrast, s/he spent all day Sunday at home. The granularity of the period was set at 24-hours. As previously stated, periods can be set at any granularity including but not limited to hours, days, weeks or months. Parameters indicating the period length, number of periods covered, and number of locations are set elsewhere; default parameters can also exist.

Figures 20, 21:
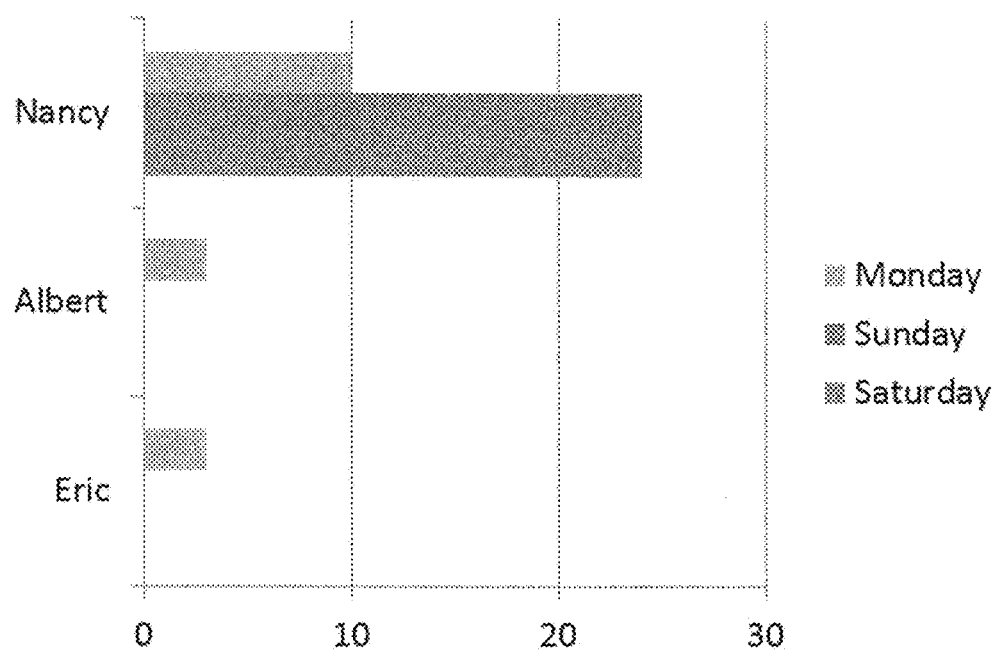
FIG. 20 illustrates an exemplary summary of top community member interactions determined according to embodiments of this invention.
FIG. 21 illustrates an exemplary summary of selected community member interactions across multiple periods determined according to embodiments of this invention.

FIG. 20 illustrates an exemplary summary of top determined community member interactions with the user being analyzed. For each top interaction listed, the corresponding total duration spent interacting with that community member over the covered time period is indicated. The number of top interactions and the period of interaction covered are parameters that can be adjusted. Default parameters are also established. As seen, the top interactions for the analyzed user were: Nancy Green, Albert Cho, and Eric Jones along with their corresponding total time spent with each interaction over a 12 hour period. Specific period ranges are selected elsewhere. The community member identity corresponds to those learned and detected. Although likely that the user analyzed interacted with both Albert Cho and Eric Jones at the same time for the same duration, this is not necessarily the case.

FIG. 21 illustrates an exemplary summary of selected community member interactions with the user analyzed across multiple periods. For each of the three community members listed (Nancy, Albert, and Eric), the total duration spent with each of them in each of the three days (Saturday, Sunday, and Monday) covered is indicated. As shown, the analyzed community member spent her/his entire Saturday and Sunday with Nancy and part of Monday with all three of the selected interacting community members. The granularity of the period was set at 24-hours. As previously stated, periods can be set at any granularity including but not limited to hours, days, weeks or months. Parameters indicating the period length, number of periods covered, and the number of locations are set elsewhere; default parameters can also exist.

Figures 22, 23:
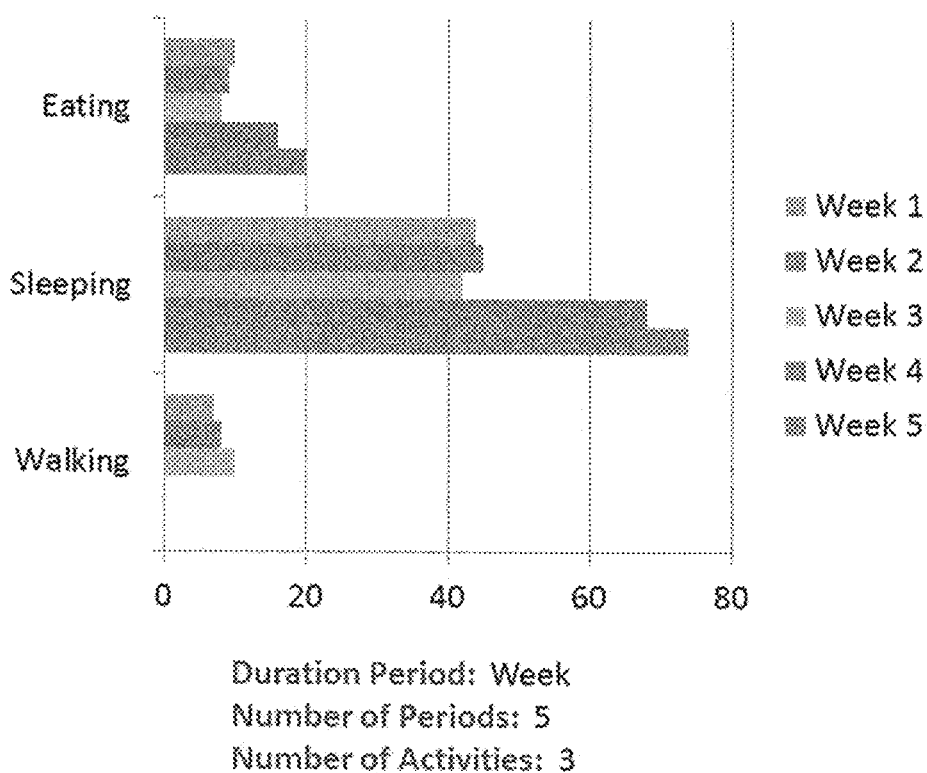
FIG. 22 illustrates an exemplary monitoring with a potential issue detected according to one embodiment of this invention.
FIG. 23 illustrates an exemplary notification list subject to suspected condition according to one embodiment of this invention.

FIG. 22 illustrates an exemplary monitoring with a potential deviation concern detected according to this invention. As shown, the granularity covered was a week, and five weeks were observed, and three activities were analyzed. In terms of walking, in weeks 1 through 3, the observed user averaged roughly one hour per day; however, in weeks 4 and 5, the observed user failed to walk any significant amount of time. Correspondingly, the observed user averaged roughly 6 hours per night sleep in week 1 through week 3, but averaged more than 9 hours per night in weeks 4 and 5. The duration of time eating likewise increased in weeks 4 and 5. Given a reduction in physical activity, a significant increase in sleep duration, and an increased appetite, an inference engine according to embodiments of this invention is likely to detect a possible onset of depression.

FIG. 23 illustrates an exemplary notification list subject to suspected conditions. The notification list is a listing of contacts, not necessarily community members, to contact should the inference engine determine that there is a sufficient change in behavioral patterns that warrant a suspicion of a condition. As shown, the identities of the differing individuals (or organizations—not shown) to be notified depending on the suspected condition are displayed. Note that the levels associated with the degree of belief in the existence of the condition determine the individuals to be contacted. The degree of belief can be, but is not limited to, an actual score or to a categorical indicator shown, such as low, medium, or high. These levels are merely predetermined thresholds, and hence, triggering conditions. Once a threshold is met, the individual(s) is/are contacted. For example, Nancy Green is contacted if a low, medium, or high level of belief is derived for sedentary, but only if the level is medium or higher for depression. In contrast, the physical therapist is only contacted for sedentary, but only if the belief level is high. Contact information for these individuals and organizations to be contacted is maintained either at the central server or locally on the device and is managed using any known in-the-art contact management approaches.

Figure 24:
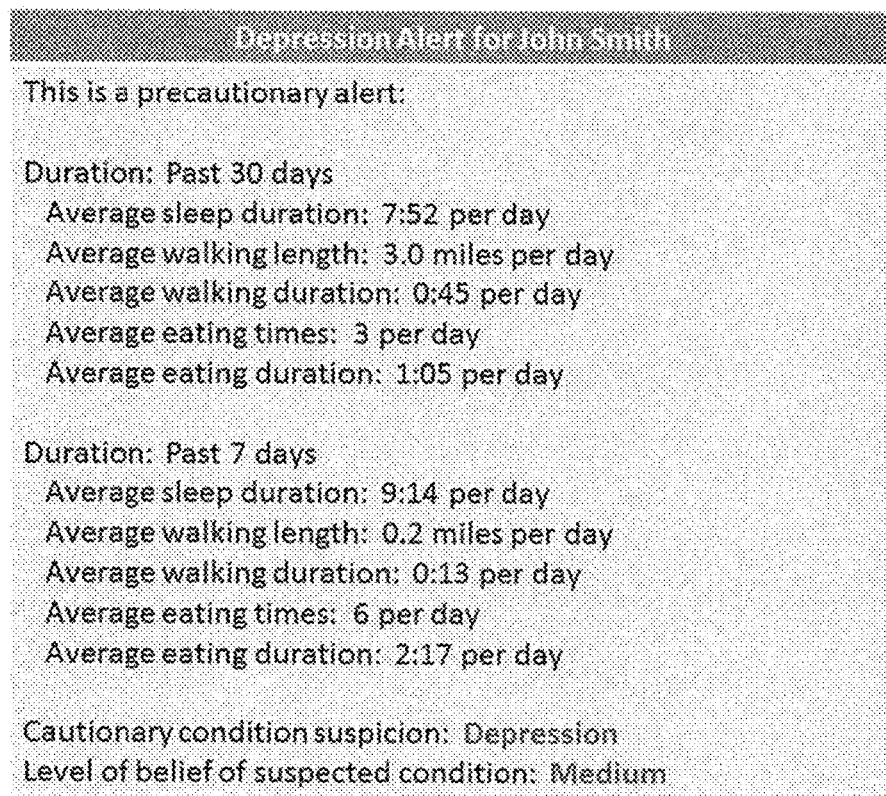
FIG. 24 illustrates an exemplary notification alert according to one embodiment of this invention.

FIG. 24 illustrates an exemplary notification alert according to one embodiment of this invention. Such an alert is sent to the corresponding contacts, shown in FIG. 23, depending on the belief level determined by the inference engine. As shown, the alert indicates past behavior, in this case the last 30 days, and compares it to more recent behavior, in this case the last 7 days. The observed metrics are noted. The suspected condition and level of support in the belief of the existence of the condition are likewise indicted. Here, the suspected condition is depression with a medium confidence level of belief.

Figure 25:
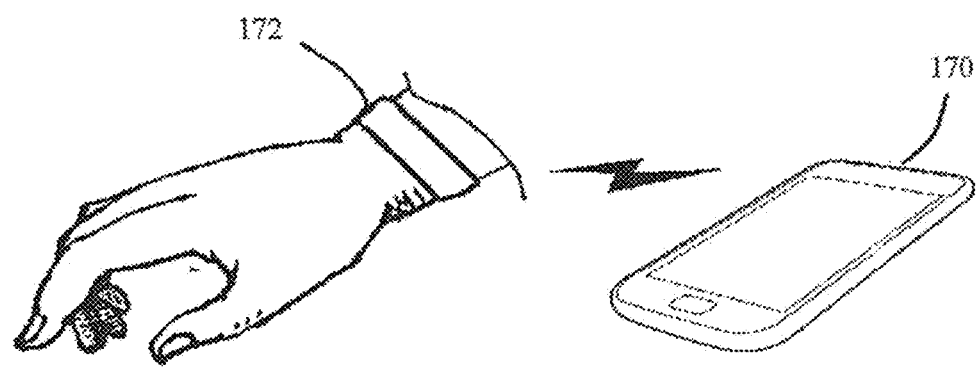
FIG. 25 illustrates smartphone and fitness tracker or other biosensor device interaction according to one embodiment of this invention.

In embodiments of the invention, the MPSM methods and systems can be combined in automated communication with electronic biosensors and/or other smartphone apps. Exemplary biosensors include without limitation wearable monitors, such as, pulse, body temperature, fitness, or other electronic body monitors, or non-wearable electronic devices such as scales or fitness machines. FIG. 25 illustrates a smartphone 170 that is a user electronic device executing the MPSM method according to embodiments of this invention. The smartphone is in wireless communication, such as using Bluetooth® or any of other similar communication protocols, with a wrist-wearable device 172, such as a fitness monitor or a smartwatch. The inference engine can consider the information about the user gathered by the device 172 in detecting, analyzing, or correlating any deviation according to methods of this invention.

The invention further includes a method of determining locations and/or activities of users participating in a social networking service. The method can be used to track members and provide reminders to the tracked user, or to provide a notification or alert/alarm to the user doing the tracking. The tracking and notification are particularly useful in monitoring health conditions and/or treatment thereof in users. In embodiments of this invention, locations and/or activities of members of a social media community are automatically and continually tracked, such as using the methods described above. The tracked location/activity information is automatically displayed for each of the plurality of members on one or more of electronic devices of the other members, depending on the particular user settings.

In embodiments of this invention, each member has the opportunity to establish a triggering condition for an other one or more of the plurality of members via her or his electronic device. The tracking system automatically monitors the one or more members for the triggering condition via the corresponding electronic device(s) of the other user. Upon automatically determining an occurrence of the triggering condition, an automated communication of the occurrence of the triggering condition is sent to the user setting the triggering condition, and any other user also added as a notification recipient.

A primary motivator for the use of MPSM systems is maintaining awareness of the current status of user's community members. Often, maintaining awareness is tantamount to knowing when a community member has met a triggering condition. Examples of a triggering condition include, but are not limited to: proximity to, arrival at, or departure from, a specified location; and/or an activity or condition of at least one of the community members automatically determined using that member's electronic device of the members, such as having a certain medical condition or engaging in a particular user activity or function. The triggering condition can be selected from automatically generated predetermined condition selections displayed in a user interface on the user electronic device, or created from predetermined templates provided to and/or created by the user.

Specified locations for the triggering conditions can be absolute or relative and/or specific or global. As used herein, absolute locations refers to specific geographic locations independent of the user, for example, an address such as 111 Chestnut Street, Chicago, Ill., while relative locations specify user related locations such as the user's "home," "work," or "favorite coffee shop." Specific locations can be absolute or relative and specify an exact location, while global locations indicate neighborhoods such as Chevy Chase, Md. Thus, triggering conditions based on locations, either absolute or relative, and/or specific or global can be set.

Some medical conditions can be determined by applications available on the mobile device. For example, applications running on mobile devices and known in the art include but are not limited to, heart rate monitoring and temperature sensing. Additionally some medical devices incorporate state of being applications. Regardless of the means by which the medically related condition is determined or tracked, triggering conditions can be specified and another user notified automatically upon the determination of the condition, or a possibility thereof.

In embodiments of this invention, the MPSM learns and derives user activities and/or locations, such as by the methods disclosed herein. Triggering conditions related to activities and/or location proximity can be set by the user or other users. For example, triggering conditions can be set by a user for the purpose of being automatically informed when a community member is automatically determined to be eating, shopping, or walking. Similarly, triggering conditions can be set for the purpose of being automatically informed when any one or more community member is automatically determined to be near the user, a location (e.g., restaurant, airport, or mall), or near another community member.

Regardless of the triggering condition set, when the community member meets the condition, the user is notified. In one embodiment of this invention, the triggering condition can be set to send the alert notification to one or more community members in addition to, or as an alternative to, the user that sets the triggering condition. Notification can be accomplished by any of the multiple known in the art notification schemes including but not limited to SMS messages, phone calls, e-mail messages, and/or application pop-ups or push notifications.

Figure 26:
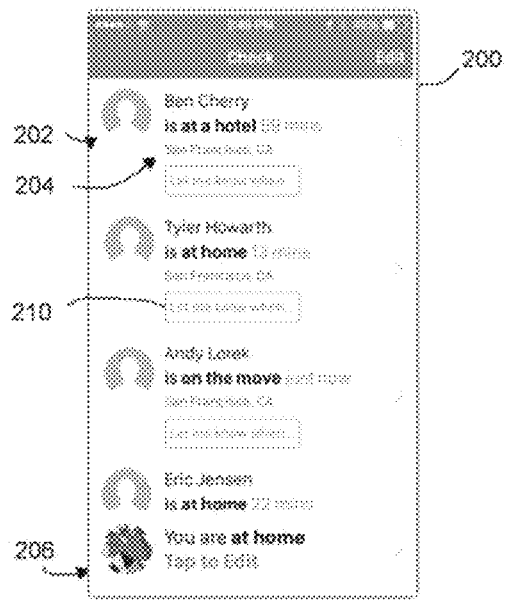
FIGS. 26-28 show mobile device screens illustrating tracking and setting triggering conditions, according to one embodiment of this invention.

FIG. 26 is a representative phone screen GUI 200 displaying a listing of community members. For each community member 202, their current personally matched user information 204, including city level geographic location, is automatically specified. Personally matched information can include, without limitation, a user activity (e.g., "on the move", playing tennis, or having coffee) and/or a user location (e.g., absolute or relative, specific or global). The duration of the current personally matched user information is likewise specified. Additionally, for each community member 202, a notification alert option button 210 is presented. This alert is set by the user for the particular community member 202 and specifies a triggering condition to be met. It is within the scope of this invention to have multiple simultaneous alerts set for a particular community member and/or for multiple community members, by the user. It is also within the scope of this invention for the user to set a triggering condition on her/himself. Once the specified triggering condition occurs, a notification is sent to the user. As shown in FIG. 26, no alert has yet been set. Also, at the bottom of the display 200, the user's current personally matched user information 206 is identified.

Figure 27:
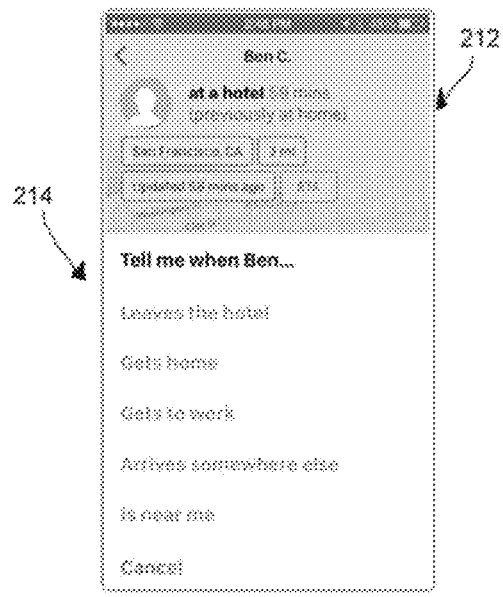
Figure 28:
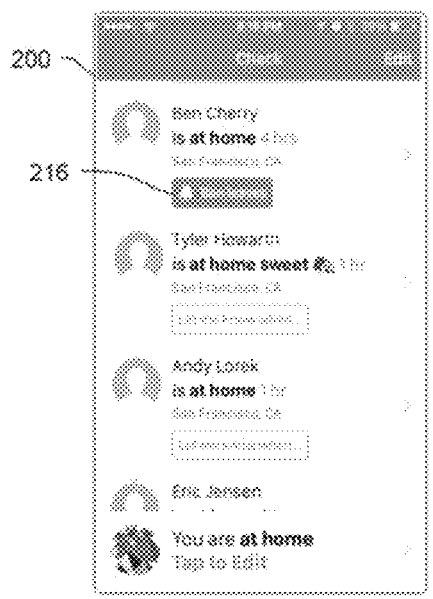

FIG. 27 shows a setting of the triggering condition, according to one embodiment of this invention. Upon selection of the button 210 associated with each community member as shown in FIG. 26, the display 212 illustrating a set of triggering conditions 214 is displayed. Also shown at the top of the display is the current matching personal information 202 for the given community member. By selecting one or more triggering conditions, alerts are set. For example, assuming a selection of "Gets home" is made, an alert is set that will automatically activate upon the system detecting the arrival of the chosen community member at his home. FIG. 28 shows the same GUI 200 of FIG. 26, only now with a set alarm condition 216.

Figure 29:
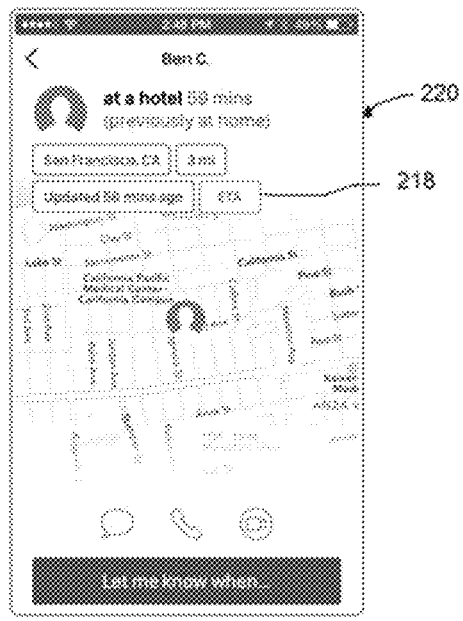
FIGS. 29-31 show mobile device screens illustrating detailed community member personally matched information according to one embodiment of this invention.

FIG. 29 shows a screen GUI 220 including more detailed community member personally matched information. Pressing the right arrow on a particular community member 202 in GUI 200 results in a display 220 that includes, without limitation, member location information, e.g., at a hotel, and duration thereof, e.g., 59 minutes, a previous location, e.g., at home, as well as additional information such as when the information was last updated. An optional map illustrating the location of the community member is likewise presented. The user has an option, by pressing the corresponding button, to text, phone, or video conference the selected community member, as illustrated at the bottom of the display. Additionally, the ETA (expected time of arrival) option can be selected. A button 210 is also displayed on this screen.

Figure 30:
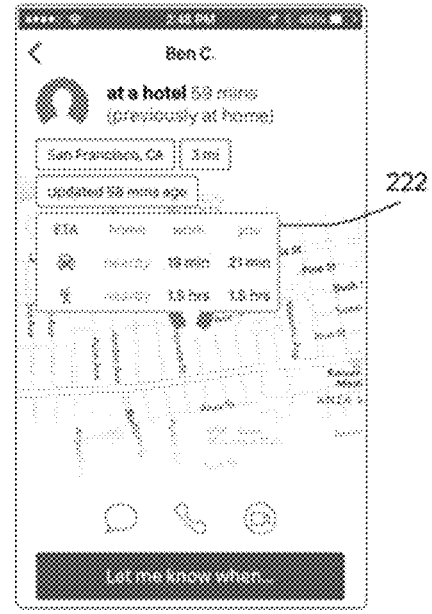

FIG. 30 illustrates an estimated time of arrival option 222 opened upon selecting ETA button 218 in FIG. 29. As shown, similar to FIG. 29, member location information, duration thereof, time of last update, and other information, including a map, is provided. However, the estimated time of arrivals for that community member to various locations and/or community members including the user using various modes of transportation is computed and illustrated. The locations illustrated can be associated to the user, to the community member, and/or any other specified location. As shown, for example, the community member, Ben C., is 19 minutes by car and 1.5 hours by foot to his work. The ETA functionality can desirably be paired with a notification of when a community member leaves a location, such as the "Leaves the hotel" notification option in FIG. 27, to predict a time of arrival for a meeting, etc.

Figure 31:
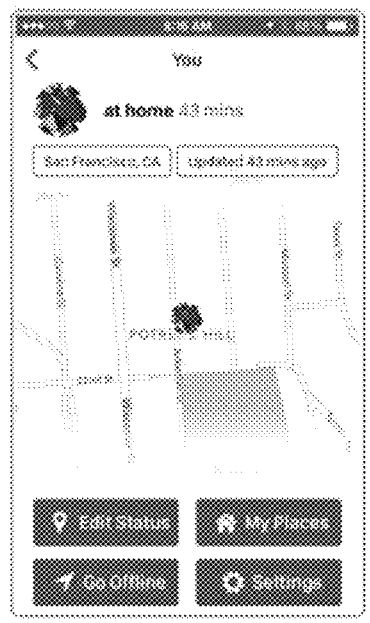

FIG. 31 illustrates detailed personally matched information for the user her/himself. As shown, the user's location and duration thereof is illustrated. Also provided are options, accessed by pressing the corresponding button, to edit the user's places, e.g., "My Places", or status, e.g., "Edit Status", alter one's settings or completely go offline.

Figure 32:
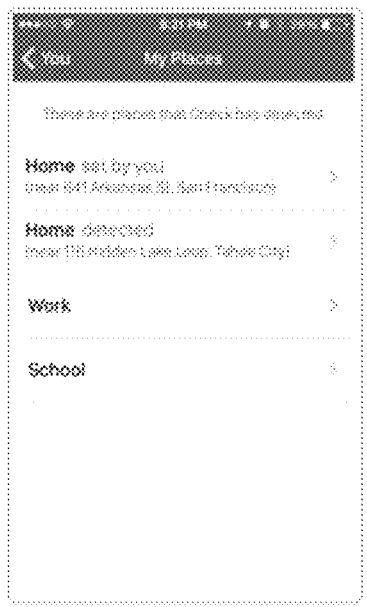
FIGS. 32 and 33 show mobile device screens illustrating user information and options according to one embodiment of this invention.

In FIG. 32, the user's "My Places" user information is illustrated and can be altered. As shown, locations associated with the user are listed. These locations were either set by a community member, including potentially the user her/himself, e.g., "Home—set by you", or automatically detected, e.g., "Home—detected". Note that these are two different home locations illustrating the option to have multiple repeated named locations. Other locations, e.g., work and school, are also shown but not specified precisely. Selecting the right arrow at each location provides for the option to specify or correct the location information.

Figure 33:
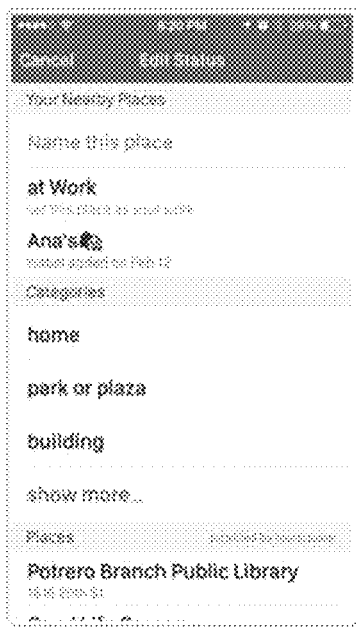

In FIG. 33, the user's "Edit Status" option is illustrated. As shown, nearby locations under "your nearby places", categories of locations, under "categories", and general places, under places, are listed. Note that other community members might set locations, e.g., Ana's home was set by Isabel. Additionally, third party location information, e.g., as provided by foursquare, can likewise be used.

Thus, the invention provides a method and system for actively monitoring for potential medical concerns based upon activity deviation and any other health related data from the electronic device or a related sensing device. The invention is based upon the methods of this invention for tracking and learning user locations and activities, and can share concerns with community members and/or health professionals. The method is executed by a computer system, preferably through a mobile device, and includes automatically monitoring learned user activity patterns.

The invention illustratively disclosed herein suitably may be practiced in the absence of any element, part, step, component, or ingredient that is not specifically disclosed herein.

While in the foregoing detailed description this invention has been described in relation to certain preferred embodiments thereof, and many details have been set forth for purposes of illustration, it will be apparent to those skilled in the art that the invention is susceptible to additional embodiments and that certain of the details described herein can be varied considerably without departing from the basic principles of the invention.

What is claimed is:

1. A method of determining health concerns of users participating in a social networking service, the method executed by a computer system and comprising:
    automatically monitoring destinations and user activities of a first user performed at the destinations via a first electronic device of the first user;
    automatically learning activity patterns for the first user;
    automatically determining a deviation in the learned activity patterns;
    automatically analyzing the deviation to identify a significance of the deviation;
    automatically correlating the significance of the deviation to a possible mental or physical health concern, wherein the automatically correlating comprises assigning a confidence metric to the possible mental or physical health concern; and
    automatically alerting a second user via a second electronic device of the possible mental or physical health concern;
    wherein analyzing the deviation comprises:
    correlating an activity decrease in the learned activity patterns to the first user being at a current destination during a first predetermined time period, and
    identifying a temporary decrease in the learned activity patterns as a function of the current destination not allowing for the activity at the destinations.

2. The method of claim 1, wherein the learned activity patterns include an exercise pattern, a sleep pattern, and an eating pattern.

3. The method of claim 2, further comprising automatically selecting the second user for alerting as a function of the confidence metric, wherein a close community member is alerted for a first confidence metric, and a medical professional is alerted for a second confidence metric, the second confidence metric being higher than the first confidence metric.

4. The method of claim 2, further comprising:
    automatically selecting a medical professional for alerting when the deviation correlates to a medical concern by including a decrease in the exercise pattern coupled with an increase in the eating pattern and an increase in the sleep pattern.

5. The method of claim 2, further comprising automatically detecting a possible onset of depression from a combination of a reduction in physical activity, an increase in sleep duration, and an increased eating pattern over the predetermined time period with a confidence metric at a predetermined high level, wherein the second user is a medical professional.

6. The method of claim 5, wherein the alerting includes a comparison of the physical activity, the sleep duration, and the eating pattern between a time period of the deviation and a second time period of predetermined duration before the deviation time period.

7. The method of claim 1, further comprising:
    automatically selecting the second user for alerting when the deviation is a decrease in an exercise pattern.

8. The method of claim 7, wherein the second user is a physical therapist treating the first user when the confidence metric is above a predetermined high metric.

9. The method of claim 7, wherein the second user is a friend having a similar exercise pattern, and the alert includes a request to engage the first user in an activity of the exercise pattern.

10. The method of claim 7, further comprising:
    automatically and continually tracking a location of an electronic device of each member of a social media community of the first user; and
    automatically alerting a community member engaged in a matching user activity to one user activity of the exercise pattern with a request to engage the first user in the matching user activity.

11. The method of claim 1, further comprising correlating the first user learned activity patterns with past and/or ongoing activities of other community users within the social networking service.

12. The method of claim 1, wherein determining the deviation comprises automatically comparing real-time data feeds from the first electronic device with historical information from the first electronic device to determine whether the first user is deviating from the learned activity patterns; and further comprising adding the real-time data to the historical information for future comparing of additional data.

13. The method of claim 1, wherein the alerting includes sending the confidence metric to the second user.

14. The method of claim 1, further comprising:
    automatically determining a second decrease in occurrences of the activity over a second predetermined time period after the first predetermined time period;
    automatically analyzing the second decrease to identify a second deviation significance; and
    automatically correlating the second deviation significance to the possible mental or physical health concern.

15. The method of claim 1, wherein the learned activity patterns comprise a communication pattern, a mobility pattern, a visitation pattern, a sleep pattern, an eating pattern and an exercise pattern, each at locations and/or with one or more community members.

16. The method of claim 15, wherein the analyzing the deviation comprises:
    correlating the deviation to user locations and conditions of the user locations during a predetermined time period; and
    identifying a temporary change in the learned activity patterns as a function of a change to a new user location during the predetermined time period.

17. The method of claim 16, wherein the analyzing the deviation comprises:
    correlating the deviation to geographic conditions of the new user location during the predetermined time period; and
    automatically identifying the temporary change in the learned activity patterns as a function of an external factor of the geographic conditions, wherein the external factor impedes the first user activity within the predetermined time period.

18. The method of claim 17, wherein the external factor comprises a weather condition at the new user location.

19. The method of claim 1, further comprising:
    receiving a triggering condition for the first user from the second user, wherein the triggering condition is the first user performing a first user activity of the learned activity patterns;
    automatically forwarding a triggered alert to the second user upon determining the triggering condition for the first user.

* * * * *